(12) United States Patent
Bechmann et al.

(10) Patent No.: US 10,286,397 B2
(45) Date of Patent: May 14, 2019

(54) PRESSING ARRANGEMENT FOR A COVER, IN PARTICULAR IN A LABORATORY APPARATUS, AND METHOD FOR PRESSURING BY USING A PRESSING ARRANGEMENT

(76) Inventors: Gregor Bechmann, Hamburg (DE); Lutz Timmann, Fuhlendorf (DE); Manuel Petzold, Hannover (DE); Stefan Roth, Hamburg (DE); Arne Schafrinski, Bad Oldesloe (DE)

( * ) Notice: Subject to any disclaimer, the term of this patent is extended or adjusted under 35 U.S.C. 154(b) by 350 days.

(21) Appl. No.: 13/401,154

(22) Filed: Feb. 21, 2012

(65) Prior Publication Data

US 2012/0270308 A1  Oct. 25, 2012

Related U.S. Application Data

(60) Provisional application No. 61/444,851, filed on Feb. 21, 2011.

(30) Foreign Application Priority Data

Feb. 21, 2011 (DE) .......................... 10 2011 011 912

(51) Int. Cl.
*B30B 13/00* (2006.01)
*B30B 15/06* (2006.01)
(Continued)

(52) U.S. Cl.
CPC . *B01L 7/00* (2013.01); *B01L 7/52* (2013.01); *B01L 2200/025* (2013.01);
(Continued)

(58) Field of Classification Search
CPC ................. B01L 7/00; B01L 2200/025; G01N 2035/0405
(Continued)

(56) References Cited

U.S. PATENT DOCUMENTS 2,951,140 A * 8/1960 Polley ..................... B65C 11/06
156/367
6,153,426 A  11/2000 Heimberg
(Continued)

FOREIGN PATENT DOCUMENTS

DE  202008009556 U1 * 12/2009 ................ B01L 7/00
EP  0955097 B1  9/2005
(Continued)

*Primary Examiner* — Michael L Hobbs
*Assistant Examiner* — Liban M Hassan

(57) ABSTRACT

The invention relates to a pressing arrangement for a cover, in particular in a laboratory thermostat, having at least: a first component disposed to exert an excitation force, a second component, in particular a plate component disposed to exert a pressing force Fz in at least one target position, a transmission device disposed for transmitting force from the first component to the second component, characterized in that the transmission device comprises a transmission component disposed to be driven by the first component and to drive the second component, and the transmission device comprises at least one elastic tensioning member disposed to be driven by the first component so as to change its tension and to drive the transmission component, and the transmission device or the transmission component causes the setting of the pressing force Fz in dependence on the target position. The invention further relates to a corresponding method for pressuring.

11 Claims, 11 Drawing Sheets

(51) Int. Cl.
  *C12M 1/40* (2006.01)
  *B01L 7/00* (2006.01)
  *G01N 35/04* (2006.01)
  *F28D 21/00* (2006.01)

(52) U.S. Cl.
  CPC ... *B01L 2300/041* (2013.01); *B01L 2300/043* (2013.01); *F28D 2021/0077* (2013.01); *G01N 2035/0405* (2013.01)

(58) Field of Classification Search
  USPC ......... 435/91.2, 287.2, 289.1, 305.4; 100/35, 100/295; 422/568
  See application file for complete search history.

(56) References Cited

U.S. PATENT DOCUMENTS

| | | | |
|---|---|---|---|
| 6,197,572 B1* | 3/2001 | Schneebeli | 435/286.2 |
| 7,570,443 B2* | 8/2009 | Blasenheim et al. | 359/822 |
| 2004/0112969 A1* | 6/2004 | Saga | B01L 7/52 236/2 |
| 2008/0318280 A1 | 12/2008 | Schafrinski et al. | |

FOREIGN PATENT DOCUMENTS

| | | | |
|---|---|---|---|
| EP | 1964609 A1 | | 9/2008 |
| GB | 2472454 A | * | 2/2011 |

* cited by examiner

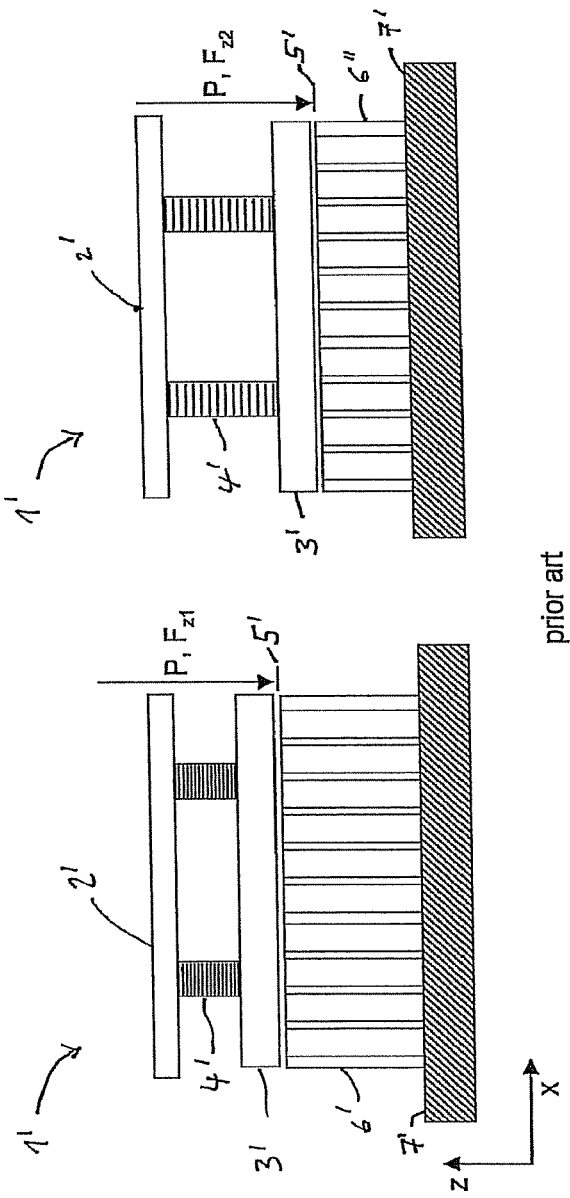

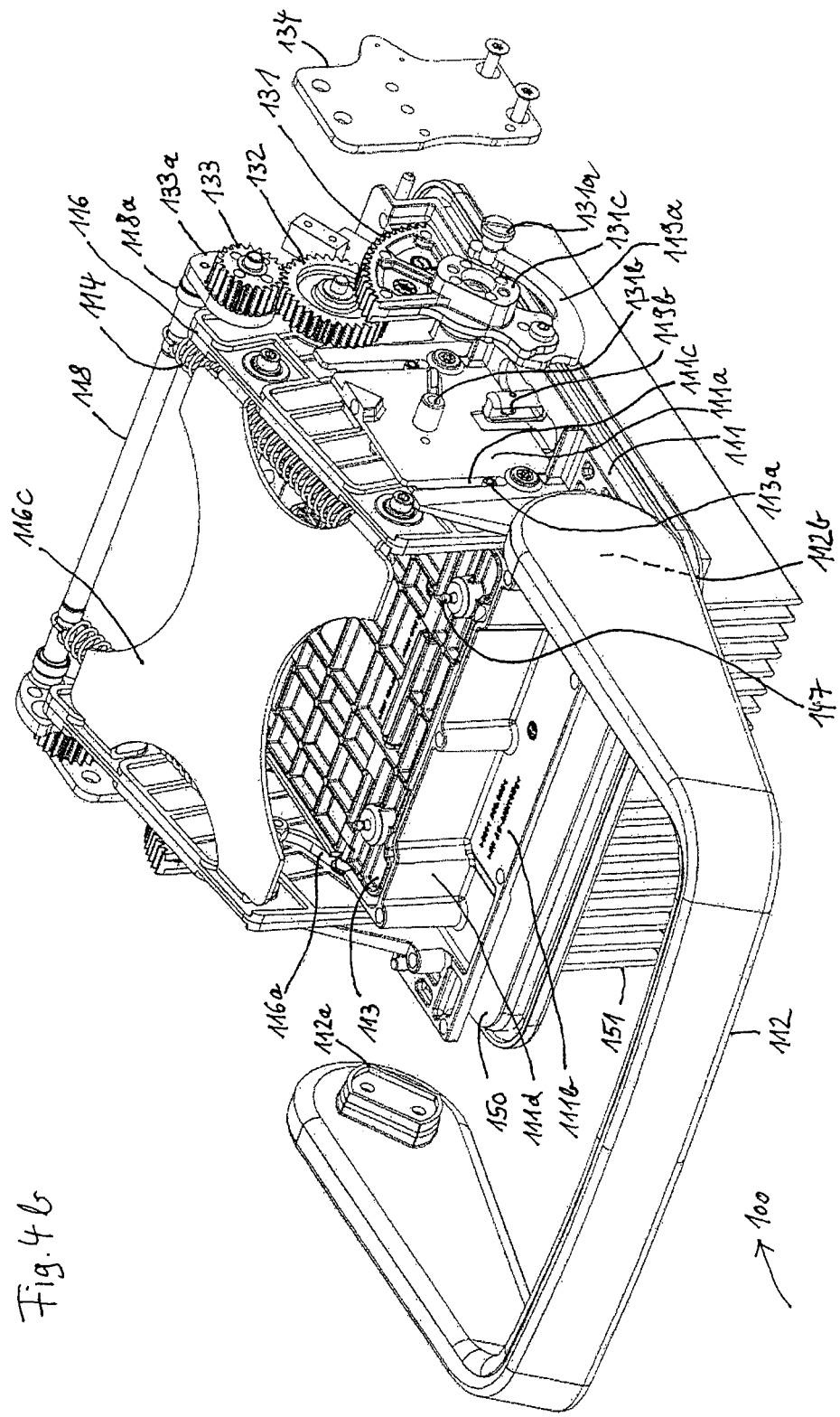

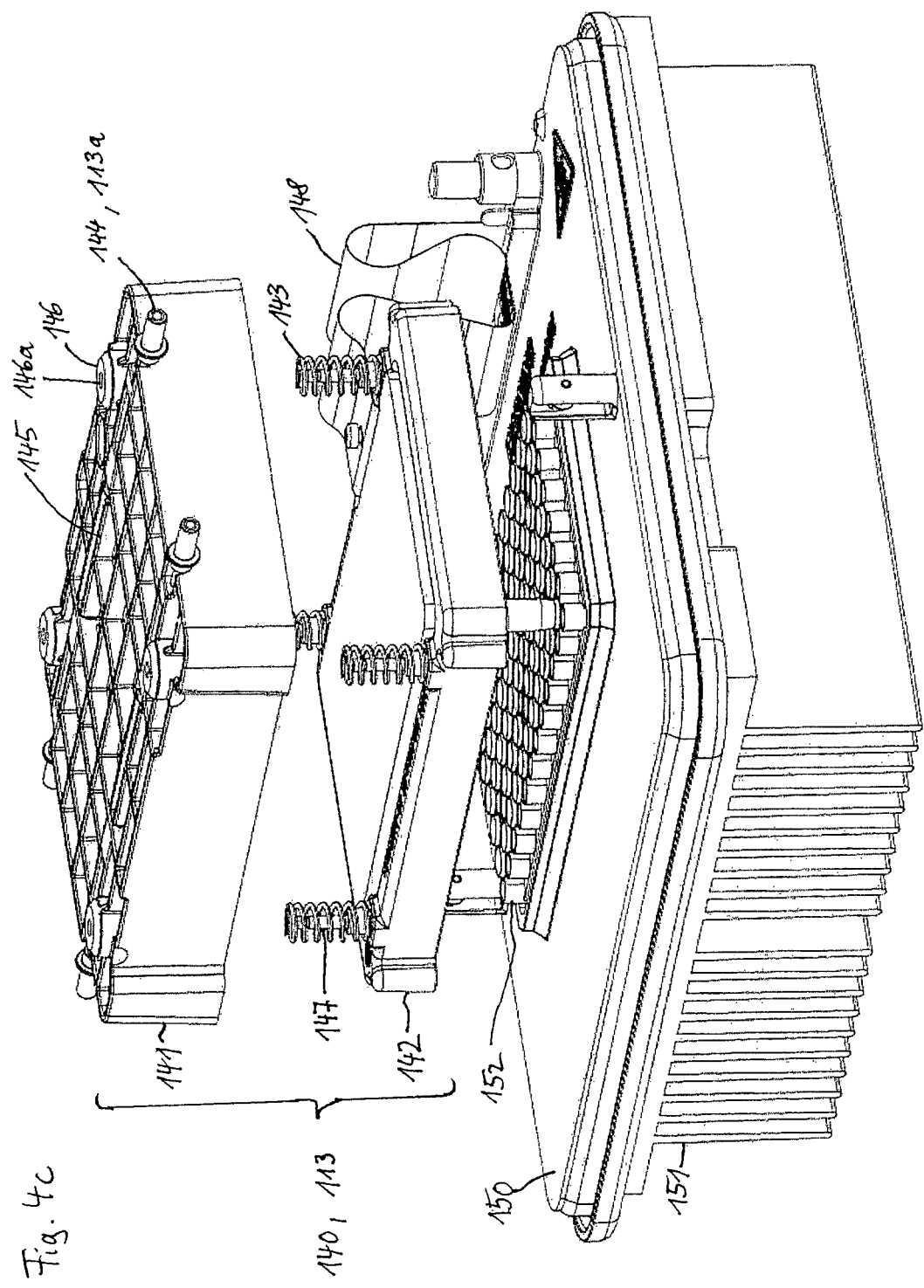

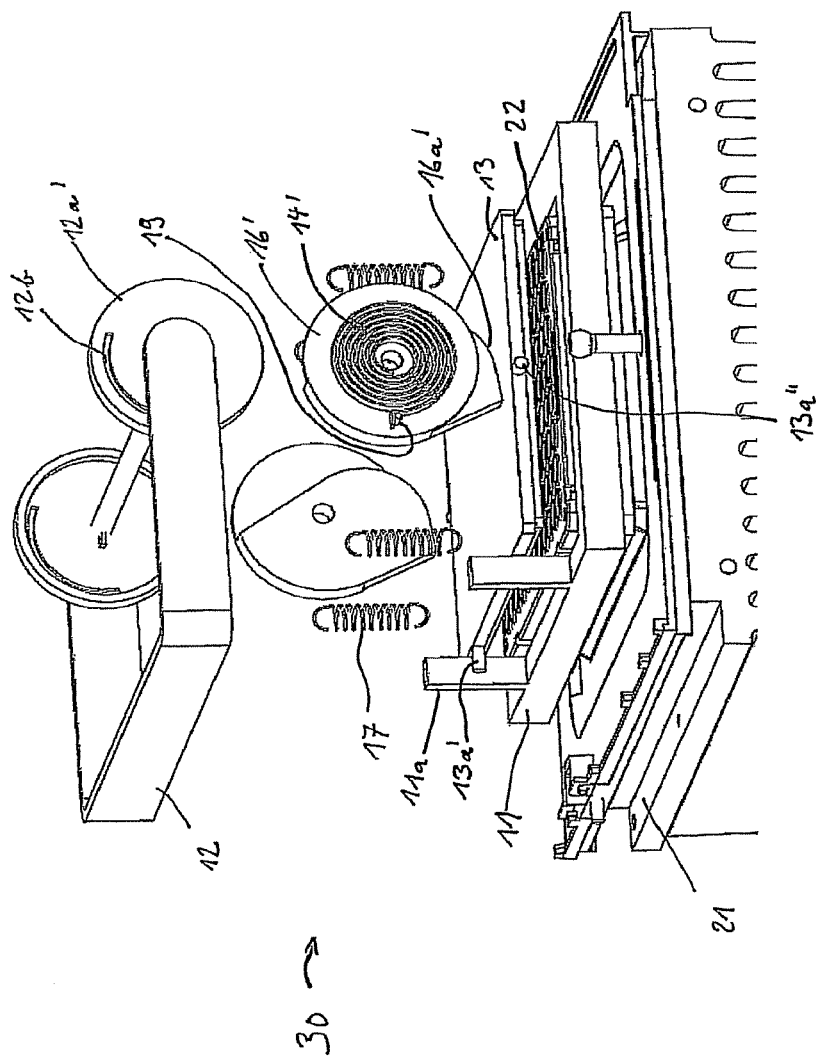

PRESSING ARRANGEMENT FOR A COVER, IN PARTICULAR IN A LABORATORY APPARATUS, AND METHOD FOR PRESSURING BY USING A PRESSING ARRANGEMENT

CROSS REFERENCE TO RELATED APPLICATIONS

This application is a non-provisional of U.S. Provisional Application No. 61/444,851, filed Feb. 21, 2011. This application claims priority to German Patent Application No. 10 2011 011 912.4, filed Feb. 21, 2011.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable.

STATEMENT REGARDING PRIOR DISCLOSURES BY THE INVENTOR OR A JOINT INVENTOR

Not Applicable.

BACKGROUND OF THE INVENTION

Field of the Invention

The present invention relates to a pressing arrangement for a cover, in particular for the cover of a laboratory apparatus, and a method for pressuring by using a pressing arrangement.

Description of Related Art

Pressing arrangements for covers are required for pressuring a target area to be covered. Although this is in particular useful for various laboratory apparatuses such as thermostats, thermomixers or thermocyclers, it may be suitable for non-tempering laboratory apparatuses carrying out e.g. optical, mechanical, or material-treating processes. These laboratory apparatuses can be found e.g. in biochemical, biological, medical, or forensic laboratories. In the case of laboratory apparatuses having a tempering function, controlled pressuring of one or more sample containers against tempered sample container receptacles may be important so as to ensure the quality, uniformity, and reproducibility of the thermal contact between the sample container and the receptacle. This is in particular the case for thermocyclers.

Thermocyclers are tempering apparatuses with which to set cyclically differing temperature stages of the samples to be tempered. Thermocyclers are in particular employed for performing polymerase chain reactions, "PCR". This reaction provides for cyclic replication of DNA by way of using products of a replication cycle requiring various temperature stages, as educts for the following cycle. The efficiency of a PCR cycle is in particular dependent on the most precise setting possible of the temperature stages in the liquid samples. PCR tends to be carried out in high-throughput screening processes. Sample plates are used, in particular microtitration plates where a plurality of sample containers, e.g. 96, 384, or 1536, are arrayed side by side. This allows simultaneous treatment of a plurality of samples, usually requiring for each of the samples to be exposed to the same temperature. This requires for each of the many containers to have identical thermal contact with the thermo block which can in particular be achieved by pressing the sample plates against the thermo block. Most thermocyclers are therefore provided with pressing arrangements having pressing plates which tend to be incorporated in the cover. The cover also serves to cover the samples to protect them from light, dust, cross-contamination and evaporating, or optionally also to additionally heat the sample containers from above.

Thermo blocks are usually provided of metal comprising an array of container receptacles corresponding to the array of a compatible microtitration plate. These microtitration plates are commercially available as disposable articles of different heights. Many conventional thermocyclers, however, require a uniform level of the surface of the sample area, i.e. of the target area or the target position for applying pressure to allow the respective pressing arrangement to function. It is therefore known to use receiving blocks of different heights or adapter plates for sample plates of different heights, which is rather work-intensive. Absent level adaptation, in these pressing arrangements different pressures would be applied to the microtitration plate in different target positions of the pressing plate in relation to the sample heights. This may result in non-uniform tempering of microtitration plates of different heights. In the case of a too low target area the pressure applied might be insufficient or non-reproducible which may result in non-uniform tempering. In the case of a too high target area the pressure applied is too high and results in mechanical tension in the sample plate, thus in inhomogeneity of contacting, or it might even mechanically damage the sample plate or the apparatus. This problem may even be reinforced with high sample containers showing a lower mechanical stability than do lower sample containers. Examples of known thermocyclers whose pressing arrangements are designed for one single level of the target area only, will be described below.

EP 0 955 097 B1 describes a thermocycler with automatic positioning of the cover which is in particular designed as a shield from light. It comprises an internal cover which is automatically positioned over the samples via a rigid mechanism. The employed type of a sample container notwithstanding, the level of the internal cover is always the same in its one only adjustable target position. The internal cover comprises at its bottom surface compression springs supporting a heated cover segment at their ends. In its end position said segment presses the sample containers to the thermo block. The pressing force is based on $Fz(z)=k*z$, wherein k is the spring constant and z is the vertical deflection of the spring from its expanded position. Fz is determined in the fixed target position by the specified spring constants of the compression springs and the level of the target area namely, the heights of the sample container top surfaces which determine the spring deflection. In terms of construction the device only allows the only one indicated curve of the pressing force as a function of z where Fz linearly increases with increasing spring deflection.

U.S. Pat. No. 6,153,426 discloses a thermocycler having a cover which is adapted to avoid great mechanical shocks in opening. In closing, the cover is locked in one only fixed target position. Its pressing arrangement provides at the bottom surface of the cover, compression springs supporting at their ends a cover segment to whose bottom surface a rubber pad is optionally fastened. In this case the pressing force is again structurally limited immediately after locking the cover in position and substantially determined by $Fz(z)=k*z$. According to this relationship the pressing force is always dependent on the heights of the sample containers.

On the other hand, EP 1 964 609 A1 discloses a thermocycler having a cover comprising a pressing arrangement the advantage of which over the known devices indicated above is in particular that it can apply a pressure independent of the heights of the sample containers. To this end the fluid-filled contact component to be pressed against the sample area is locked in the target position in contact with the sample area by means of a fixing mechanism and thereafter the pressure on the fluid is built up. The fixing mechanism which is variable in height avoids the build-up of different pressures dependent on the target position of the contact component as it is the case with the other prior art devices indicated. Setting the pressure in dependence on the target position is not described in, nor sought by, EP 1 964 609 A1.

BRIEF SUMMARY OF THE INVENTION

It is the object of the present invention to provide an improved pressing arrangement for a cover which in particular offers more flexibility in designing the pressing force in dependence on the target position.

DETAILED DESCRIPTION OF THE INVENTION

According to the invention a pressing arrangement is provided for a cover, in particular in a laboratory thermostat, having at least: a first component disposed to exert an excitation force, a second component, in particular a plate component disposed to exert a pressing force Fz in at least one target position, a transmission device disposed for transmitting force from the first component to the second component, characterized in that the transmission device comprises a transmission component disposed to be driven by the first component and to drive the second component, and the transmission device comprises at least one elastic tensioning member disposed to be driven by the first component so as to change its tension and to drive the transmission component, and the transmission device or the transmission component causes the setting of the pressing force Fz in dependence on the target position.

The pressing arrangement according to the invention offers the advantage that the pressing force Fz applied to the second component is in particular not limited to those pressing forces based on $Fz=k*z$, as is the case with the known devices indicated above but it offers greater flexibility in design. Herein, k is a constant and z the deflection of an elastic tensioning member, e.g. a screwed spring or spiral spring provided e.g. with a linear force/path characteristic. In the present invention at least one elastic tensioning member is used for storing the excitation energy and thus causing a pressing force on the adjacent target area. The arrangement according to the invention will be more flexible over the known devices with compression springs in particular because the elastic tensioning member is preferably not immediately coupled to the second component with which the force is applied to the target area. Instead the invention preferably provides a transmission device having a transmission component which is (indirectly or directly) driven by the elastic tensioning member. Only the additional transmission component allows the transformation of the force applied by the tensioning member. This allows to configure a pressing force Fz dependent on the target position the path of which can be influenced by way of a great variety of means which are preferred embodiments of the pressing arrangement according to the present invention. The terms used and preferred embodiments of the invention will be described below.

The pressing arrangement is preferably disposed at or mounted to a laboratory apparatus, in particular to a cover area of a laboratory apparatus. The laboratory apparatus is preferably a thermostat or thermocycler which is preferably suitable or configured for performing PCR, or e.g. an apparatus performing optical or electric methods or measurements. The laboratory apparatus preferably comprises in operation a fixed-position or variable-position target area on which a pressing force is applied by means of the pressing arrangement. Preferably the laboratory apparatus comprises a sample receiving area to receive a liquid, solid, gaseous or other sample. The sample receiving area may be configured to receive one or more sample containers or it may immediately receive samples. The sample receiving area may in particular comprise a thermo block with which to temper samples, e.g. the thermo block of a thermocycler. Preferably the target area is disposed at this sample receiving area.

The pressing force Fz serves to apply a pressing force to a target area. This target area is a side namely, a contact side, in particular outside surface, of a contact segment which is preferably disposed at a sample receiving area. The pressing arrangement is preferably configured to contact this contact side of the contact segment to apply a pressing force to this outside surface. The contact segment may be configured integrally with another component, in particular the sample receiving area, or it may be a separate or detachable component. Preferably the target area is configured such that it can be contacted in at least three points or a plurality of, points or sections, in particular planar sections of the second component of the pressing arrangement or another component of the pressing arrangement. This allows to pressure a flat, in particular substantially planar target area very uniformly.

Preferably the target area and a pressing area of the pressing arrangement, in particular of the second component, are substantially configured planar, wherein it is e.g. possible for a plurality of projection sections or depressions to be provided in this planar area which may be interconnected so as to form e.g. a grate. This allows to apply increased pressing force in spots or sections. The orientation of the target area is preferably such that when the laboratory apparatus is used as intended said target area or planar area is disposed horizontally, or perpendicular to gravitation which extends in the negative z direction. Or else, this orientation may extend in another direction.

The target area may be a covering component of a sample receptacle, of a single-sample container or a multi-sample container, e.g. a microtitration plate or a PCR plate, it may comprise at least one covering component or it may be formed by a covering component. In particular though not exclusively in the case of microtitration plates, PCR plates and other multi-container arrangements the covering component may be a covering film, or a sealing film which may be transparent, or it may be a container cover, in particular a container cover integrally connected or connected, or else unconnected, with the sample receptacle or the sample container. The covering component may further be or comprise a plate or pad which is in particular elastically deformable, may in particular consist of, or comprise, silicone. The covering component may comprise a holding frame holding e.g. a film or a pad or a plate. The covering component may furthermore comprise multiple container covers that are fixedly connected, i.e. separable destructively only, disposed e.g. as cap strips.

The pressing force Fz is preferably selected so as to achieve a uniform thermal contact between a sample plate with containers, e.g. a microtitration plate, and the receiving area of a sample container receptacle block, e.g. a thermo block. Preferably it should furthermore be achieved that the single covers of the individual sample containers are sufficiently pressed against the respective sample containers to prevent foreign matter, e.g. dust, vapor, gases or liquids, from entering into the container interior and in particular to prevent evaporation of liquid samples from the container. The respective pressing force Fz is preferably, in dependence on each target position, between 50 N and 350 N, between 100 N and 350 N, or between 150 N and 250 N.

The invention in particular relates to the cover of a laboratory apparatus, in particular of a thermocycler, for pressuring a plate component against a sample area of the laboratory apparatus to be covered, wherein the cover comprises a pressing arrangement according to the invention. The pressing arrangement is in particular described with reference to a cover. This cover may e.g. be a hinged cover which cover can be opened and closed by way of pivoting about an axle. To this end the pressing arrangement preferably comprises at least one hinged portion which together with another hinged portion operates as a hinge. The complementary hinged portion may be disposed on a base belonging to a laboratory apparatus, e.g. a thermocycler. The hinge may be characterized by at least one hinge axle preferably disposed on a horizontal plane, e.g. the x-y plane of a Cartesian coordinate system.

For the present invention, the z-axis of a Cartesian coordinate system defines the "upwardly" direction, i.e. in the direction of the positive z-axis extending preferably parallel to the vertical and to gravitation. "Downwardly" means in the direction of the negative z-axis.

The cover may be a sliding cover. The cover preferably comprises at least one slide portion or track portion allowing a sliding movement of the cover by means of which the sliding cover can be opened and closed. A cover is understood to mean any device covering a target area in a covering position. The covering may be direct such that no other component is disposed between the target area and the cover. Or else, covering may be indirect such that at least one other component, e.g. a sealing pad, a grate, or a plate is disposed between target area and cover. The cover or an optional supporting device, in particular a carrier component of the pressing arrangement, may be disposed at least in part or entirely stationary, i.e. immovable relative to a base in at least one, in multiple, or in all of the degrees of freedom and to this end may interact e.g. with at least one fastener which may be fixedly connected with a base and or the cover and/or the pressing arrangement.

The cover or the pressing arrangement may comprise a locking device for locking the cover (or the pressing arrangement) in a locking position which may e.g. be the closed position of the cover. The locking device may comprise mechanical and/or (electro) magnetic locking components. In this way the cover is secured in the locking position. Or else the locking device may be configured to employ the locking as an abutment for applying the pressing force or another force. Preferably the locking device is coupled with the excitation movement such that transferring the first component from the first to the fourth position, which will be described below, causes automatic locking. This is preferably achieved by mechanical and kinematic coupling of the excitation and locking movements but it may as well occur e.g. electrically.

The pressing arrangement preferably comprises a supporting device which supports or carries in particular the first component, the second component and/or the transmission component.

The pressing arrangement can preferably be operated manually. In particular can the pressing arrangement preferably be operated manually such that it does not require e.g. any electrical energy supply for exerting the pressing force. This allows a more flexible use of the pressing arrangement, in particular independently of current supply. The pressing arrangement or the transmission device is preferably configured to be mechanical, and/or in particular does not require any electrical energy source.

Or else it is possible and preferred for the pressing arrangement to be manually operated in part or motor-operated in part, e.g. by being provided with means for triggering the pressing force or means for supporting a pressing force that is driven manually in part. This allows to make operating the pressing arrangement still more comfortable. Or else the pressing arrangement may be operated fully automatically, e.g. computer-controlled. The pressing arrangement may comprise means for automatically performing an excitation movement, e.g. an electric motor for automatically applying the excitation force.

The first component of the pressing arrangement may be, or comprise, a manually operated operating member. The operating member is disposed at the pressing arrangement preferably for rotary, translational, or combined rotary/translational movement. Preferably the operating member is a lever or a stirrup that pivots or rotates around a pivot axis. The first component may further comprise an operating member, preferably an operating lever or grip member, for partially or completely manual application of the excitation force and/or an excitation movement.

The first component is preferably configured for carrying out an excitation movement and disposed movable. "Disposed movable", in the scope of the present invention means that a component of the pressing arrangement is disposed to be movable relative to another component of the pressing arrangement, in particular relative to the preferably provided supporting device. The excitation movement causes movement of the first component between two positions which are referred to as the third position and fourth position of the pressing arrangement. The excitation movement is preferably translational, rotary, or translational and rotary combined.

The first component is preferably disposed such that the excitation movement can always be performed from the third position up to the fourth position substantially independently of a target position or stop position of the second component wherein the stop position is in particular that position in which the second component is blocked in its pressing movement. This offers the advantage that the user does not need to decide on the extent of the excitation movement, thus facilitating operation. Furthermore, in the case of an automated or partially automated realization of the excitation movement, automatic selection of an excitation section can be simplified in that the excitation movement stops automatically due to being stopped in the third or fourth position, e.g. by way of a stop switch. In this way any more complicated devices for determining the position, in particular sensor equipment, may optionally be dispensed with. In particular in combination with the feature that the transmission device or the transmission component causes setting the pressing force Fz in dependence on the target position, the advantage or feature is obtained that the pressing arrangement is in particular configured for automatically setting the pressing force Fz in dependence on the target position. Preferably no further settings by the user are then required for applying a suitable pressing force on a specific, current target position. This considerably facilitates operation of the pressing arrangement. It is conceivable, however, for the pressing arrangement to be provided with additional influencing means for the user to influence the pressing force Fz to be applied. This means may e.g. comprise an adjusting screw, calibrating components, or other actuators. This provides more flexibility in using a pressing arrangement, in particular a substantially automatic pressing arrangement.

The second component of the pressing arrangement preferably is or comprises a plate component with which to exert pressure on a plane- or grate-like target area. The second component is, however, not limited to plate-like members. The second part may comprise means for heating and/or cooling, in particular tempering means suitable for controlled heating and/or cooling. The tempering means may be Peltier elements, a heating film or conveyor sections, e.g. tubes, for conveying a tempering tempering agent. Furthermore the second component preferably comprises at least one temperature sensor to allow temperature control for the second component. An electronic control device which in particular allows temperature control may be disposed at the pressing arrangement, in particular at the second component. The second component preferably is, or comprises, a plate provided to be tempered or heated. The plate may comprise a transparent covering plate allowing visual observation of the target area to be covered, in particular of fluorescent samples. This is an option e.g. for "real-time" PCR where the progress of the PCR reaction is observed by way of changes to fluorescence emission of the samples.

The second component is a component, in particular a plate component, disposed for exerting a pressing force Fz on a target area in at least one target position. The target area includes a variable position namely, this variable target position. It is preferably variable in height, i.e. taking a specific position along the z-direction of a Cartesian coordinate system. It is e.g. conceivable for first sample containers, e.g. a first microtitration plate, to show a lower total height than do second sample containers. The second sample containers may be higher than first sample containers e.g. by a factor c. The factor c may lie between 1.0 and 5.0, between 1.0 and 3.0, between 1.0 and 2.0, or between 1.5 and 2.0. Then it is required in the case of the first sample containers lower in total height, to position the second component at a lower level for applying the pressing force than in the case of the second sample containers. The pressing arrangement is preferably configured for automatically setting the pressing force Fz in dependence on the sample height, i.e. without requiring the user to adjust the pressing force or other actuators.

The second component preferably comprises a primary segment and a secondary segment. The primary segment is preferably coupled with the secondary segment via an elastic spring device such that pressing movement of the primary segment causes the secondary segment to perform a smaller movement. The elastic spring device comprises at least one elastic spring component, in particular comprising 2, 3, 4 or more elastic spring components. The pressing movement causes deformation of the elastic spring components. By way of providing the spring components a uniform transmission of the pressing force of the second component to the target area is achieved. In particular a substantially planar contact surface of the second component or the secondary segment rests in parallel and planar on a likewise substantially planar contact surface of the target area which causes uniform pressuring of the contact surfaces. As has been described above, this contact surface may be defined by a multitude or plurality of elevations or depressions the arrangement of which may be aligned e.g. with the layout of the container array of a microtitration plate. The force which the primary segment receives as the pressing force from the transmission device is the force which the secondary segment receives from the primary segment via the spring device and transmits it as a pressing force to the target area Therefore the spring device does not substantially complicate determining the desired function Fz(z) for the pressing force.

In the scope of the present invention the expression "component x is designed (or configured) for the purpose y" means that the component x comprises technical means realizing the purpose y. These means may be structural components, e.g. mechanical or electrical components, e.g. circuits, or it may comprise software or computer code. The specific configuration of this means may be left to the knowledge of the skilled person or will be described in more detail.

Preferably the transmission device is configured to transform the force transmitted by the tensioning member and to transmit it to the second component as a transformed force. Force transmission occurs according to a transmission function allocating to each value of an excitation force a value of a transformed force. The transformed force is preferably the press-on force Fz. Each value for the transformed force is preferably dependent on the currently applied target position. The transformation of the force transmitted to the tensioning member allows to impose a desired curve on the transmitted force and/or to allocate to the transformed force a dependence on the target position z. In particular can this target position z be the level of the target area, e.g. the stop position, i.e. the position on the z-axis of a Cartesian coordinate system.

The transmission device comprises at least the elastic tensioning member and the transmission component wherein preferably the first component, the tensioning member, the transmission component and the second component are connected, preferably connected in this sequence, preferably connected as a force transmission cascade, and/or are preferably kinematically coupled. Force transmission cascade means that the transmission of an excitation force or other force to the first component causes it to transmit a force in at least one position, preferably continuously at least in sections, to the next member in the force transmission cascade namely, the tensioning member, which then in turn transmits in a similar way this or another force to the transmission component which then transmits a new force to the second component. The force transmission cascade may comprise other "members" namely components forwarding a force. Kinematic coupling means in the present case that the movement of one of the components affects or causes movement of the other of the components. In this way the pressing force can be configured as desired, in particular can a pressing force Fz(z) be caused which is not or not solely dependent on the deflection z of the tensioning member from its rest position according to $Fz(z)=k*z$.

The first and second components and the transmission component are preferably disposed on the pressing arrangement to be movable relative to one another.

Performing a movement of the second component serving for pressuring the second component against a target area, is presently referred to as a pressing movement. Preferably the second component is disposed movably for performing a pressing movement in particular with reference to the pressing arrangement or its optional supporting device. The pressing movement is preferably linearly translational, in particular in parallel to the z-axis, and preferably moves the second component downwardly in the negative z-direction. Preferably the second component is disposed at the pressing arrangement to be movable between a first position and a second position, in particular starting from the first position up to a stop position of the second component, the stop position being in particular that position in which the second component in its pressing movement is blocked in at least one direction, thus e.g. by way of being stopped in the target position in the target area. By way of the translational pressing movement a uniform stopping can be achieved which is advantageous if the second component is configured planar, e.g. as a plate component, against a planar target area, e.g. a sample plate. Or else the pressing movement may be configured different, preferably partially or entirely rotary.

The pressing arrangement or the transmission device is preferably configured to be mechanical, and/or in particular does not require any electrical energy source.

The elastic tensioning member is preferably a spring or preferably comprises at least one spring. This spring is preferably an extension spring or a compression spring, thus offering a good combination with a translational excitation movement. The tensioning member or the spring may be connected with the first component at one of its ends by means of a rope member or otherwise connected or coupled with the first component, e.g. by means of a gear transmission which preferably comprises one or more gear wheel members. The spring is preferably a coil spring, in particular a torsion spring or a leg spring. Or else the spring may be a spiral-shaped spring transmitting a torque. This offers a good combination with a rotation-type excitation movement. Spiral-shaped springs offer the advantage that their force/path characteristic may be configured linearly over a wide deflection range. This is preferred since it allows easier determination of the desired force transmitting function. Preferably two springs or a larger number of springs are provided for achieving e.g. in the case of multiple hinge points a uniform force transmission of the first component to the transmission component. A tensioning member is a component showing a force/path characteristic wherein preferably path changes cause force changes or tension changes. Although the force/path characteristic of the tensioning member is preferably linear, it may be different, e.g. respectively substantially degressive, progressive, and in particular continuous or discontinuous.

The transmission device preferably comprises at least one transformer section, preferably 2, or else 3, 4, 5, 6 or more transformer sections, which may in particular be disposed at the transmission component which in particular transforms the force transmitted by the tensioning member and transmits it to the second component as a transformed force, preferably as this pressing force. Although said transformer section is preferably disposed at this transmission component, it may be partially or entirely disposed at another component, e.g. the second component.

The transmission component is preferably a non-elastic, preferably rigid, preferably manufactured integrally, in particular milled, cast, or stamped component. The transmission component is preferably a rod-like or plate-like component disposed translationally movable at the pressing arrangement. The transmission component is furthermore preferably a plate-like or non-platelike component disposed rotationally movable at the pressing arrangement. The transmission component is preferably movably disposed at the pressing arrangement for performing an intermediate movement between a fifth position and a sixth position. The transmission component preferably transmits an excitation force and an excitation movement into a transformed force and an intermediate movement by way of which the pressing force is preferably caused. The transmission component is preferably disposed at the pressing arrangement for moving the second component in the direction of the target position. Preferably the pressing arrangement comprises exactly two transmission components or multiple transmission components to be able to transmit e.g. a force still more uniformly.

The transformer section is preferably a curved guide section or comprises a curved guide section. The curved guide section preferably comprises a curved-track shaped design which serves to guide a guided component along such curved track which may be achieved by way of this component gliding or rolling along this curve. The curved guide section is preferably disposed to be driven by the tensioning member, effecting the press-on force of the second component by means of a positive guide along a curve. The curved guide section furthermore preferably comprises a curved track-shaped projection, surface or edge, a curved track-shaped depression or slot, in particular a pivoted link, eccenter or a variable-pitch thread, in particular a multiple-pitch thread.

Preferably at least one guide member preferably coupled with the second component is provided. It is preferably configured to be guided or positively guided by the curved guide section. The curved guide section is preferably configured for guiding or positively guiding the guide member. The guide member may be a pin member, in particular a cylindrical pin which may be integrally or completely fixed to the second part. The pin member may comprise a rolling section with a rotary roll or roller or a slide section to allow or facilitate rolling or sliding along the curve. A curved guide section may e.g. be defined such that it comprises at least one guide member to be guided along a curved track. In geometric inversion the transformer section, e.g. the curved guide section, may be provided to be disposed at the second component and the guide member, e.g. the pin, at the transmission component.

The curved guide section allows to transmit an excitation force "Fa" to a transformed force by means of a geometric relative arrangement of two components. This is exemplarily explained by way of FIG. 3. Presently a first component transmits in a linear excitation movement along the x-axis an excitation force $Fa=k*\Delta x$ to the tensioning member. The latter transmits the excitation force and in a contact point at the curve applies a normal force $Fnormal=Fa/\sin \alpha$ to the curved track of the transmission component. Herein, $\alpha$ is the angle of the tangent at the curve in the contact point. When the transmission component is movable only along the z-axis, then it is pressed downwardly by the portion $Fz=Fa/\tan \alpha$, corresponding to the z-component of the vectorial normal force. Thus this force is dependent on the angle. When the contact point glides along the curve or the contact point position changes, e.g. due to a different height of the target area, then the amount of Fz will likewise change. In this way the pressing force can be set by means of the curve guide by adjusting the path of the curved track as desired.

The transformer section is, however, not limited to a realization by means of the curved guide section but it may comprise means which transmit an input force, e.g. the excitation force, in an output force, e.g. the pressing force, e.g. stepping up and/or stepping down. The transformer section preferably comprises mechanically acting means to in particular realize a fully mechanically acting transmission. Or else the transformer section may comprise other force transmitting means, e.g. hydraulic or electrical means to realize e.g. an electrically controlled force transmission by means of an electrically controlled or selected actuator, in particular a piezo-electric component.

Preferably the transmission device, in particular the transformer section, is configured such that in various target positions z of the second component, which may in particular correspond to positions along the z-axis, the pressing force Fz shows a specified amount which is determined by the configuration of the transmission device, in particular of the transformer section, and which follows at least one function Fz(z) in particular at least in sections. It is e.g. preferred for Fz to be substantially constant at least in sections, i.e. in the scope of a tolerance t, i.e. Fz=c, where c−t<c<c+t, thus preferably t<0.1*c or 0.05*c or 0.01*c), where c is a real number and may show a physical dimension, e.g. Newton. With Fz(z) being constant or constant in sections, this offers the advantage of a constant pressing force for a specific level area of the target positions. The width of the section showing a constant pressing force is preferably adapted for a constant pressing force to be applied to a specific range of target positions. Then the same pressing force will always act e.g. on relatively low types of microtitration plates. Similar presentations will follow later.

Preferably the transmission device, in particular the transformer section, is configured such that in different stop positions of the second component the pressing force is constant within a tolerance range, the stop position being in particular that position in which the second component is blocked in its pressing movement in at least one direction.

Preferably the transformer section, in particular the curve of a curved guide section, is configured such that a higher pressing force substantially acts for lower target positions than for higher target positions, "higher target position" meaning a target position showing a larger z value relative to the z-axis of a Cartesian coordinate system. Correspondingly the transformer section, in particular the curve of a curved guide section, is preferably configured such that a lower pressing force substantially acts for higher target positions than for lower target positions. This structure causes gentle treatment of or preventing mechanical overload on e.g. higher sample container groups, e.g. higher microtitration plates which are mechanically less stable than are lower sample container groups. Or else it is possible and preferred for the transformer section, in particular the curve of a curved guide section, to be configured at least in portions such that a lower pressing force substantially acts for lower target positions than for higher target positions.

Preferably the function Fz(z) shows between the first and second positions at least in portions or entirely, a gradient different from zero such that the first derivative of Fz(z) following z does not equal zero, thus d/dz (Fz(z))< >0. Furthermore the function Fz(z) shows, preferably between the first and second positions at least in sections or entirely, a variable gradient such that the second derivative of Fz(z) following z is different from zero, thus d2/dz2 (Fz(z))< >0. This is in particular how the force transmission can attain the desired curve.

Preferably the transformer section or the curve defines between the first and second positions a first, in particular a lower curved guide section following a first function, e.g. z=fz1(x; y) which is a curve z in dependence on x and/or y, and also defines a second, in particular upper curved guide section following a second function, e.g. z=fz2(x; y) wherein preferably the gradient in the second curved guide section is larger than or equals each of the gradients in the first curved guide section, i.e. e.g. d/dx fz2(x)>=d/dx fz1(x) (x, y, and z being the respective coordinates in the Cartesian coordinate system). In particular in this way can it be achieved that in the case of lower-level target positions higher pressing forces can be applied than in the case of higher-level target positions. It may e.g. be provided to pressuring by means of the second curved guide section, sample containers showing a second height that is higher by a factor c than containers showing a first height which are pressured by means of the first curved guide section. The factor c may e.g. lie between 1.0 and 5.0, between 1.0 and 3.0, between 1.0 and 2.0 or between 1.5 and 2.0.

Generally speaking, the transmission function Fz(z) (presently, z is the target position or the Cartesian z-coordinate, pressing force Fz) or the curve function z=fz(x; y) (x, y, z being the coordinates in the Cartesian coordinate system) can be determined by way of calculation or simulation. In this respect reference is made to the exemplary embodiment in FIG. 7.

Preferably the transmission device, in particular the transmission component, the transformer section—and/or at least in portions the curved guide section—are configured such that the pressing force Fz1 resulting from the force transmission in these first target areas z1 showing a smaller distance a1 from the second position p2, is larger than the pressing force Fz2 in second target areas z2, showing a larger distance a2 from the second position p2 (z, z1, z2, p1 (position 1), p2 (position 2) presently represent a value of the positive Cartesian coordinate z>0, thus smaller z-values indicate "lower"), thus Fz1(z1)>Fz2(z2) wherein p2<z1<p2+a1<p2+a2<z2<p1, a2>a1. This allows e.g. to apply to higher-level container arrangements, e.g. microtitration plates, which may show reduced mechanical stability, a lesser force Fz2 than to lower-level container arrangements. The latter may require a larger pressing force Fz1 since they tend to contain a large plurality of sample containers, e.g. 96, 384, 1536, thus also tending to have a larger contact surface over which the pressing force is distributed. This is significant e.g. in view of the sealing effect of the pressuring because with the contact surface increasing, the ratio of pressing force to contact surface will decrease.

Preferably the force Fz1(z1) is substantially constant in the area z1, i.e. constant within a tolerance, as has been indicated above. In this way, lower-level container arrangements are subjected to a substantially constant force. This is often desired since e.g. lower-level microtitration plates often come in slightly different total heights wherein the number of containers is constant and thus the contact surface or press-on surface remains constant, thus allowing or requiring a constant press-on force. An exemplary embodiment thereof will be described below by way of FIG. 7.

What is also considered inventive is—in particular with reference to the features described above and below—a laboratory apparatus having a pressing arrangement or a pressing arrangement, in particular in a laboratory thermostat, the pressing arrangement comprising at least: a first component disposed for applying an excitation force, a second component, in particular a plate component disposed movable at least between a first position p1 and a second position p2 for applying a pressing force Fz in at least one target position z, a transmission device disposed for the transmission of force from the first component to the second component, characterized in that the transmission device is configured such that the pressing force Fz1 resulting from the force transmission in those first target areas z1 showing a smaller distance a1 from the second position p2, is larger than the pressing force Fz2 in second target areas showing a larger distance a2 from the second position p2, thus in particular $Fz1(z1)>Fz2(z2)$ wherein $p2<z1<p2+a1<p2+a2<z2<p1$, $a2>a1$. In particular: z, z1, z2, p1 (position 1), p2 represent a value of the positive Cartesian coordinate $z>0$, thus smaller z-values indicate "lower-level"). Preferably the force $Fz1(z1)$ is substantially constant in the area z1, i.e. constant within a tolerance, as has been indicated above.

Other than a mechanical solution for configuring the transmission device comprising e.g. as described, at least one transmission component and/or at least one tensioning member, other mechanical and/or partially mechanical or electrically operating solutions are conceivable, e.g. wherein the pressing arrangement or the laboratory apparatus provided with the pressing arrangement comprises an electrical control device which may comprise a micro controller and which e.g. by means of sensors detects the target position and in dependence thereon exerts a predetermined, desired pressing force (depending on the target position) e.g. by means of an actuator driven electrically or otherwise. The pressing arrangement, the cover provided with the pressing arrangement or the laboratory apparatus equipped with the pressing arrangement are preferably configured to automatically set the target position-dependent pressing force Fz, in particular Fz1 and/or Fz2, in particular without requiring user action for specifying the amount of the pressing force in that the target position z is a stop position of the second component at the target area, with the stop position of this stopper serving either immediately as the end point of a force transmission cascade from the first component via the transmission device to the second component, as it is the case e.g. with the mechanical solutions described. Information about this stop position may preferably also be captured and utilized to select the predetermined pressing force Fz, in particular Fz1 and/or Fz2 dependent on such information, and to have the pressing arrangement apply said pressing force to said target area. Capturing may occur by means of an electrical position sensor, information may be processed by a control device and stored in a memory device, e.g. RAM, ROM, EEPROM, etc., for retrieval, and predetermined pressing forces or functions Fz(z) may be readily stored in a memory as observational pairs or otherwise.

The pressing arrangement preferably comprises a supporting device and preferably a guiding device connected therewith by means of which the second component can be, or is, guided preferably translationally between the first and second positions at the supporting device such that the pressing movement is a linear movement. It is preferred for the excitation movement to cause the translational, rotational or combined translational/rotational intermediate movement of the transmission component or another component of the pressing arrangement, and for the intermediate movement to perform this linear pressing movement. The pressing arrangement is preferably configured such that the second component and the target area translationally move toward one another—relative to one another—during such pressing movement in that e.g. the second component moves in the direction of the target area (may be different—e.g. inverse) that the pressing movement substantially terminates by the stopping of the second component and of the target area and that substantially from such stopping the press-on force is transmitted or applied.

The first and second components and the transmission component are preferably made of metal, in particular of steel or aluminum or an alloy of such metal. Plastic material may be employed as well. The pressing arrangement preferably comprises a housing surrounding the pressing arrangement at least in part or substantially completely.

In a first preferred embodiment the pressing arrangement comprises a supporting device, e.g. a supporting frame on which the second component is supported for performing a vertically downwardly pressing movement, the tensioning member in particular comprising a screwed spring which is e.g. connected with the first component at one of its ends and e.g. connected with the transmission component at the other of its ends, the transmission component being a plate component that is horizontally movable in particular in the direction along the x-axis of the coordinate system, and is supported on the supporting device vertically upright and comprises at least one curved guide section with which to positively guide a guide member connected with the second component, such that the second component, being driven by the horizontal movement of the plate component, performs the vertical pressing movement.

In a second preferred embodiment the pressing arrangement comprises a supporting device on which the second component is supported for performing a vertically downwardly pressing movement, the tensioning member comprising a rotary spring or spiral spring which is e.g. connected with the first component at one of its ends, e.g. connected with the transmission component at the other of its ends and is rotatably supported in an x-z-plane of the coordinate system about an axle parallel to the y-axis, the transmission component being an eccentric member supported on the supporting device rotatable about an axle parallel to the y-axis of the coordinate system and comprising at least one curve guiding edge with which to positively guide a guide member connected with the second component, such that the second component, being driven by the rotational movement of the eccentric member, performs the vertical pressing movement.

In a third preferred embodiment the pressing arrangement comprises a supporting device on which the second component is supported for performing a vertically downwardly pressing movement, the tensioning member comprising a rotary spring or spiral spring which is e.g. connected with the first component at one of its ends, e.g. connected with the transmission component at the other of its ends and is rotatably supported in an x-y-plane of the coordinate system about an axle parallel to the z-axis, the transmission component comprising an eccentric member rotatably supported on the supporting device about an axle parallel to the z-axis of the coordinate system and comprising multiple eccentric threaded portions each of which positively guiding a guide member connected with the second component, such that the second component, being driven by the rotational movement of the eccentric member, performs the vertical pressing movement.

The invention further relates to a method for pressuring a component, in particular a plate component, against a target area, in particular a sample area, by means of a pressing arrangement, in particular the pressing arrangement according to the invention, the pressing arrangement comprising at least a first component, a second component, in particular a plate component, and a transmission device comprising a transmission component and at least one elastic tensioning member, the method in particular comprising the features:

transferring the second component to a target position;
exerting an excitation force by means of the first component;
transmitting the force from the first component to the second component by means of the transmission device so as to exert a pressing force by means of the second component;
driving the transmission component by means of the first component and preferably driving the second component by means of the transmission component;
causing a tension change of the tensioning member by way of driving the first component;
driving the transmission component by means of the tensioning member; and
applying the pressing force Fz in dependence on the target position of the second component.

The method comprises preferred configurations which can be derived from the description of the pressing arrangement according to the invention and its preferred configurations or optional functions. The definitions of terms and explanations of components and means apply to all the subject matter according to the invention, i.e. the pressing arrangement and the method for pressuring, unless a different description is given or the context indicates otherwise. Features of the subject matter and embodiments according to the invention may be combined where it appears conceivable or advantageous. Solutions for the transmission of force or movement between components of the pressing arrangement and its described configurations based on geometric and/or kinematic inversion of the presently described force and movement transmission mechanisms but which substantially show an effect according to the invention e.g. the function of force transmission Fz(z) or Fz1($z1$)>Fz2($z2$), are likewise inventive.

Further preferred embodiments of the pressing arrangement according to the invention and the method according to the invention can be taken from the following description of the exemplary embodiments in conjunction with the figures and the description thereof. Identical components of the exemplary embodiments are substantially designated by the same reference numerals, unless a different description is given or the context indicates otherwise. The figures:

BRIEF DESCRIPTION OF THE SEVERAL VIEWS OF THE DRAWING(S)

FIGS. 1a and 1b show a known prior art pressing arrangement, in the case of a higher-level target position (FIG. 1a) and a lower-level target position (FIG. 1b).

FIGS. 2a and 2b schematically show a first exemplary embodiment of the pressing arrangement according to the invention, in the case of a higher-level target position (FIG. 2a) and a lower-level target position (FIG. 2b).

FIG. 4b shows in an isometric, exploded view the pressing arrangement of FIG. 7a in the second, lowered pressing position of the second component.

FIG. 4c shows in an isometric, exploded view the structure of the second component of the pressing arrangement of FIGS. 7a and 7b.

FIG. 5b shows in an isometric, exploded, oblique rear view, the pressing arrangement of FIG. 5a, in the second, lowered pressing position of the second component.

FIGS. 1a and 1b show a known pressing arrangement 1' according to the prior art, in the case of a higher-level target position (FIG. 1a) and a lower-level target position (FIG. 1b). In the case of the higher-level target position an excitation movement P and excitation force Fa convey the first component 2' to the illustrated end position wherein the compression springs 4' showing the spring constant k are deflected namely, compressed by a distance $\Delta z1$ from their expanded position. The springs transmit the excitation force as a pressing force Fz to the second component 3', a pressing plate 3'. This results in a first press-on force according to Fz1~k*$\Delta z1$. In the case of the lower sample height in FIG. 2, where the first component is also conveyed to the same end position, the deflection of the springs out of their expanded state is weaker namely, by $\Delta z2 < \Delta z1$. This results in a lower second press-on force Fz2~k*$\Delta z2$, where Fz2<Fz1. In these devices which have already been explained initially, the pressing force Fz is always dependent on the target position according to Fz~k*$\Delta z$, thus e.g. on the surface level of the sample plate 6', 6", which is held by the holding plate 7'. With the end position fixedly specified, these devices in particular do not allow transmission of a transmission function Fz(z) (z the position on the z-axis of the Cartesian coordinate system) in which Fz($z2$)>Fz($z1$), in the case of the two target positions z1, z2 of the second component 3': z2<z1 (z1, z2 being Cartesian coordinates).

Figure 2B:
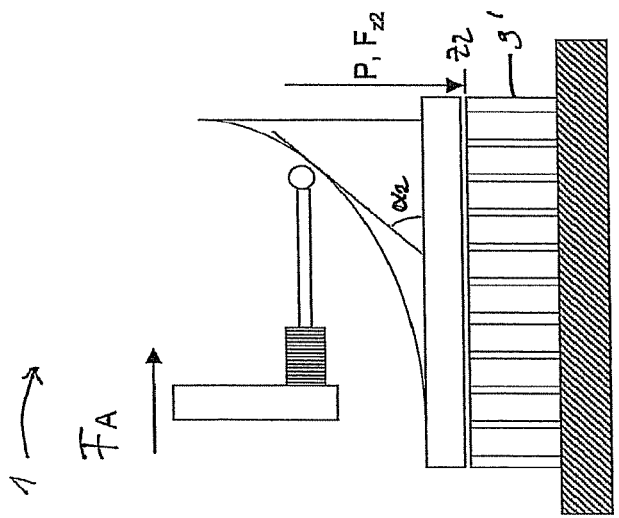
Figure 2A:
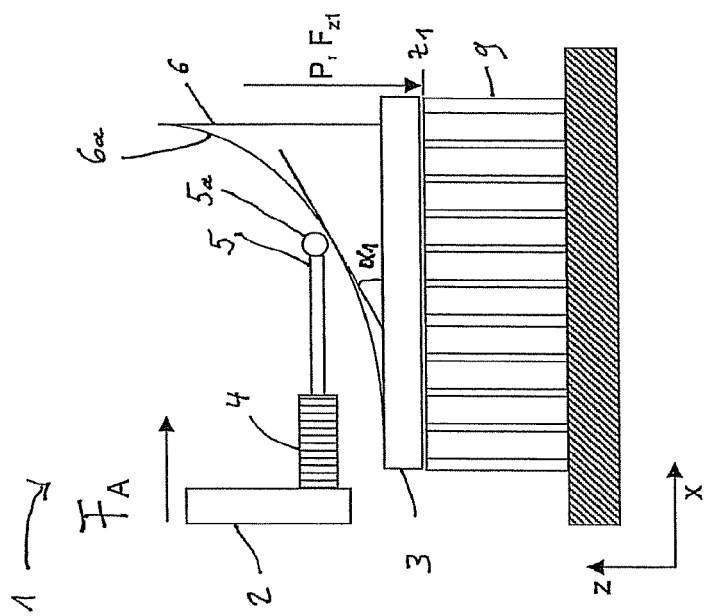

FIGS. 2a and 2b schematically show a first exemplary embodiment of the pressing arrangement 1 according to the invention, in the case of a higher-level target position z1 (FIG. 2a) and a lower-level target position z2 (FIG. 2b). In both of the FIGS. 2a and 2b the pressing arrangement, in particular the second component 3, has first been aligned in the respective target position z1, z2 where z1>z2 in the target area namely, on the surface of the respective sample plate 9, 9'. In FIG. 2a the first component 2 was transferred from a position with the compression spring 4 expanded, referred to as the "third position" (not shown) to a position with the compression spring 4 compressed, referred to as the "fourth position" (shown). In FIG. 2b the x-value of this fourth position is different from that in FIG. 2a while the z-value is the same.

Figure 3:
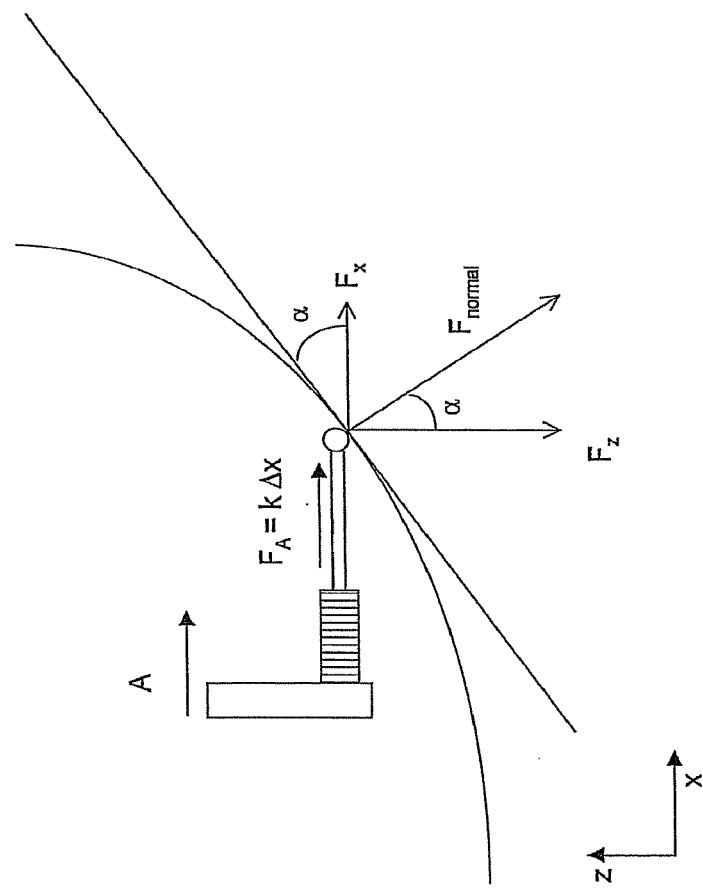
FIG. 3 shows a diagram to explain the force transmission in the example of FIGS. 2a and 2b.

The first component 2 transmits an excitation force to the compression spring 4. The compression spring 4 presses with its rigid end component 5, one end of which being rigidly connected with the compression spring 4 and the other end of which supporting a slider component 5a, against a contact point on the curved track 6a of the transmission component, transmitting a transformed transmission force to the transmission component 6. In the contact point a normal force acts on the transformer section 6a namely, the curved track section of the transmission component 6 which in the present example is fixedly connected with the second component 3. The pressing force Fz is determined by the deflection of the compression spring 4 from its expanded position and the angle α of the tangent of the contact point of the slider component 5a on the curved track 6a. Fz1 is different from Fz2 since the deflections of the compression spring 4 and the angles α are different. In this way the arrangement geometry of the first component 2 and the second component 3 and the transmission component 6, in particular of the transforming section 6a, allows to specify the desired pressing force. FIG. 3 shows a diagram explaining the force transmission in the example of the FIGS. 2a and 2b, which was already explained above.

Figure 4A:
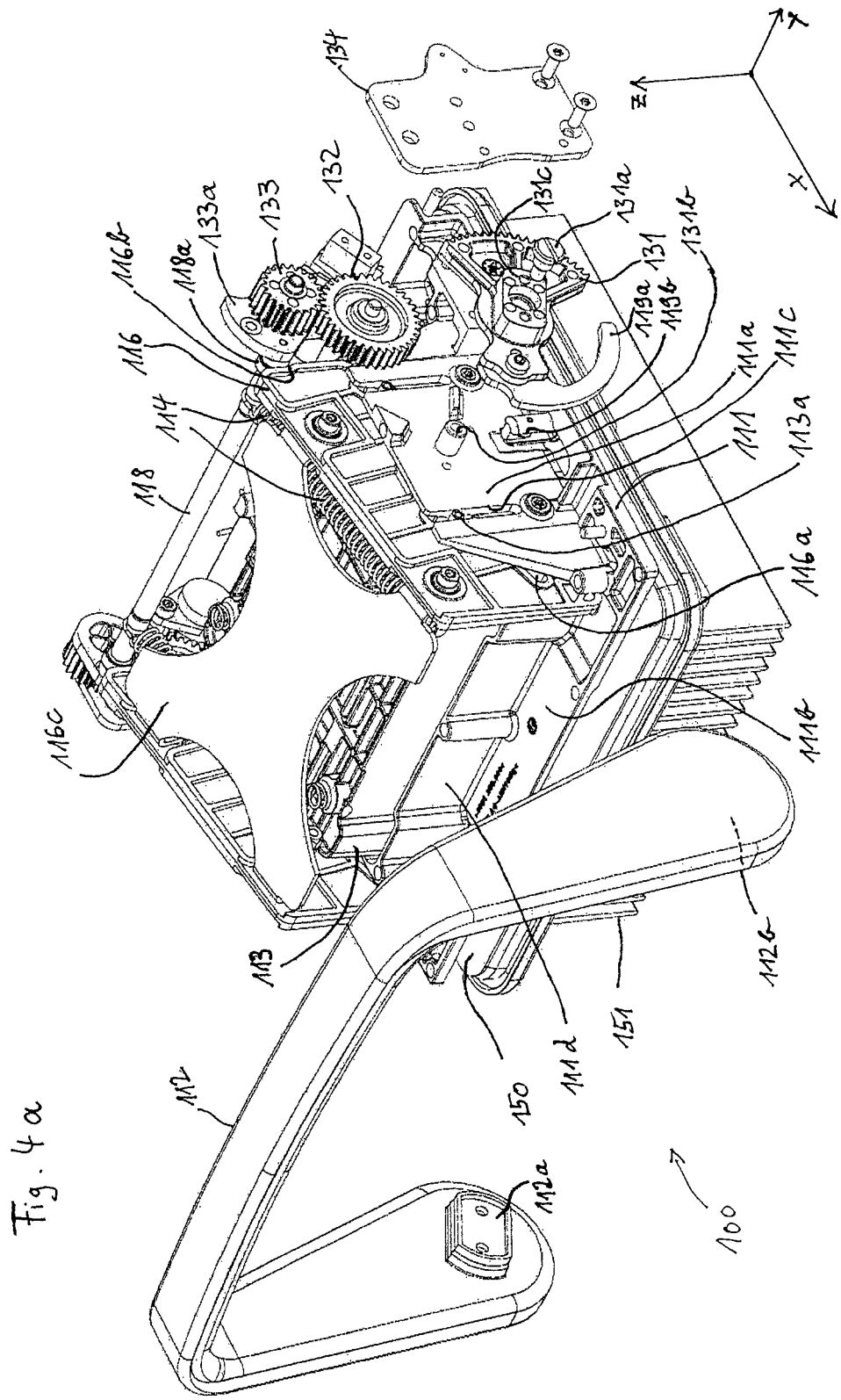
FIG. 4a shows in an isometric, exploded view another exemplary embodiment of the pressing arrangement according to the invention according to the first preferred embodiment in the first, lifted position of the second component.

FIG. 4a shows the pressing arrangement 100 according to the first preferred embodiment, in the first, lifted position p1 of the second component which is configured as a pressing plate 113, in an exploded view. The pressing arrangement 100 is presently an element of a hinged cover or of a thermocycler, which is presently not shown completely to render the elements of the pressing arrangement and the cover better visible. The hinged cover is shown in the closed state in which the base plate 111b of the supporting frame 111 of the hinged cover is arranged horizontally above the likewise horizontally arranged worktop section 150 of the thermocycler. With the cover opened, the worktop section 150 is largely accessible to the user for loading the receiving section which is located centrally in the worktop section 150 and which may e.g. be configured as a silver thermo block with a microtitration plate which may e.g. be loaded with PCR samples and covered with a sealing film. In the state as shown the hinged cover covers the worktop section 150, in particular its thermo block with the microtitration plate but it is not yet locked in position. A tempering rib arrangement 151 disposed on the bottom surface of the worktop section 150 extends downwardly serving for heat exchange between Peltier elements (not visible) and the ambience, if the thermo block needs to be quickly brought to other temperatures in any PCR cycle.

The first component of the pressing arrangement 100 is the lever 112 which the user transfers manually from the position shown in FIG. 4a namely, the described third position, to the fourth position (FIG. 4b). Setting the pressing force Fz occurs automatically in dependence on the target position. Independently of the target position, i.e. independently of the height of the microtitration plate inserted or the height of the target area defined by the upwardly contact surface of the sealing film, and independently of the pressing force Fz applied to the target area, the user always applies the pressing force by the same excitation movement from the third to the fourth position, by means of an excitation force Fa. The pressing force is thus applied automatically without requiring the user to consider the dosage of the pressing force, thus providing very comfortable use.

The lever 112 shows two opposite, mirror-image fastening areas 112a and 112b by means of which the lever 112 is attached to respective fastening sections 131c of a gear wheel segment 131. Corresponding to this articulation the transmission device is arranged for the transmission of the force from the lever 112 to the pressing plate 113 in two substantially mirrored force transmission paths. The excitation force is transmitted via a gear transmission 130 to the bearing rod 118 where one end each of a screwed spring 114 serving as a tensioning member is supported. With the other of its ends the screwed spring 114 is connected with a transmission component 116 such that the excitation movement of the lever 112 causes intermediate movement of the transmission components 116. Due to the two force transmission paths an increased excitation force may be caused to be still more uniform than in the case of one force transmission path only, which is likewise conceivable.

The gear transmissions 130 each comprise a gear wheel segment 131 that is rotatably supported on the lever hub 131b by means of the screw 131a. The fastening section 131c has the lever 112 fastened to it. The gear transmission causes a transformation of the first excitation movement namely, of the first excitation movement of the lever 112 with the gear wheel segment 131 rotating less than −90°, into a second excitation movement performed by the smallest gear wheel 133 where the smallest gear wheel rotates approximately −240°. Both FIGS. 4a and 4b show the correct angular positions of the lever 112 and the gear wheels 131, 133, even if due to the exploded view the lever and the gear wheel segment 131 are illustrated removed from their correct positions. The gear wheel segment 131 visible in FIGS. 4a and 4b and the smallest gear wheel 133 move, to the observer, counterclockwise and the medium gear wheel 132, clockwise as the user moves the lever 112 in the x-direction and downwardly to apply the pressing force. The vertical plate 134 fixedly attached to the supporting frame 111 serves as a bearing for the rotational axes of the gear wheels 132, 133.

The smallest gear wheels 133 each have attached to it a cantilever plate 133a to which the bearing rod 118 is eccentrically fastened, distanced from the rotational axis of the gear wheel 133. The counterclockwise rotation of the smallest gear wheel 133 causes rotation of the bearing rod 118 in the same sense. Then the bearing rings 118a attached to the bearing rod 118 glide or roll downwardly along a vertical outside surface of the transmission component 116. To overcome the threshold 116b of the outside surface of the transmission component 116 this movement must displace the transmission component in the x-direction. The resistance thus defined by way of the threshold 116b determines an arresting position of the lever 112 in its upright position (FIG. 4a) which signals in particular to the user that the third position has been attained or overcome.

The gear wheel segment 131 further has a circular-arc hook member 119a attached to it which, as the lever 112 is brought down, engages in an abutment component 119b belonging to the base component of the thermocycler so as to lock the cover or the supporting frame 111 of the cover. The abutment component 119b and the lever hub 131b are substantially vertically aligned on top of one another so as to have the retaining force of the locking device acting substantially in parallel to the vertical (z-direction). In this way, stress due to the retaining force on the hinge of the hinged cover in the x-direction is avoided for a more uniform transmission of the retaining force and thus also of the pressing force to the target area. Preferably the abutment component 119b is further disposed so as to lie in the plane perpendicular to the pressing plate 113, substantially halving the same, which plane lies parallel to the y-z-plane in the FIGS. 4a and 4b. This causes the pressing plate 113 to apply uniform pressure on the target area. This locking device serves among other things as an abutment when applying the pressing force of the pressing plate 113 to the target area at the thermocycler. Due to the kinematic coupling of the locking device with the transmission device the excitation movement thus effects a simultaneous locking movement so as to dispense with a separate locking action.

The bearing rod 118 rotation about the axis of the smallest gear wheel 133 causes a deflection of the screwed spring 114 in the negative x-direction starting from a predefined position of the bearing rod. This causes the transmission component 116 to be likewise urged in the negative x-direction.

The transmission components 116 are rib-stabilized transmission plates arranged upright, parallel to the x-z-plane and translationally and glidingly movable relative to the supporting frame 111 in the x-direction. Both of the transmission plates 116 are fixedly connected via the covering component 116c, their movements thus being coupled so as to achieve more uniformity and greater ease of operating the pressing arrangement. The vertical outside surface on which the bearing rod 118 glides is the side of the transmission plate 116 not visible in FIGS. 4a and 4b, lying substantially parallel to the y-z-plane and the normal vector of which substantially points in the negative x-direction.

Figure 7:
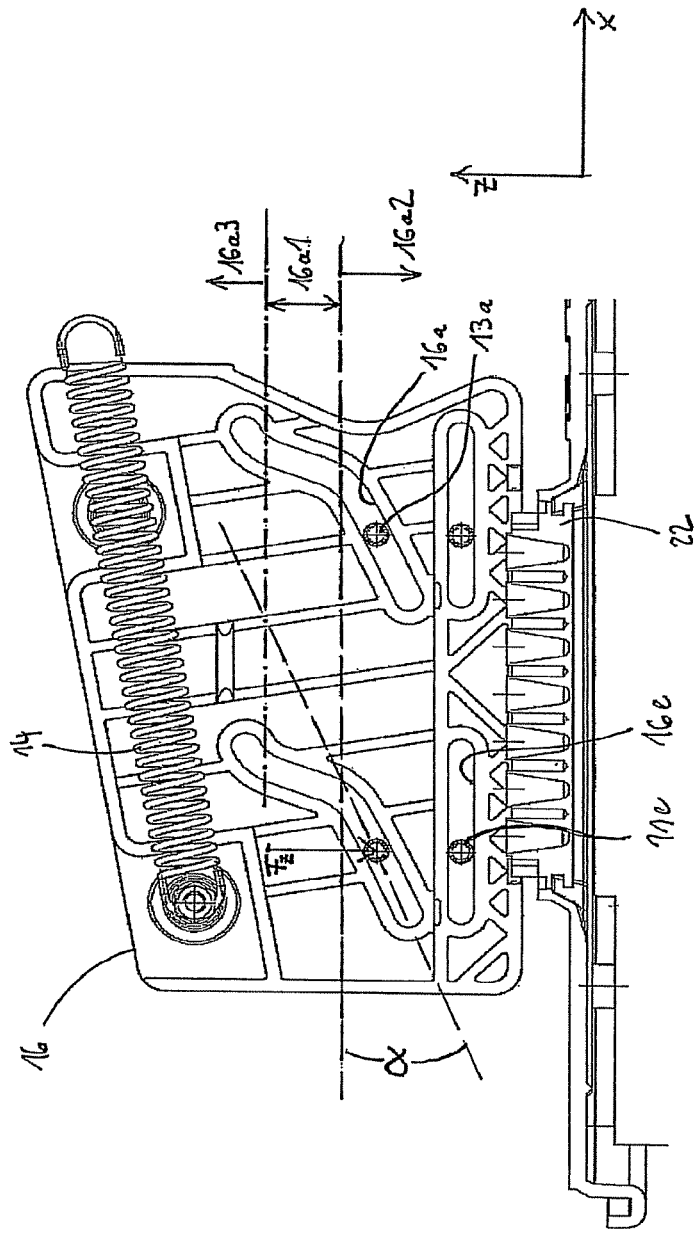
FIG. 7 shows the transmission member according to an exemplary embodiment of the pressing arrangement according to the invention where the shape of a curved track is determined and specified by way of calculation.

The transmission plate 116 is further referred to as curve plate since it is provided with a pair of slide slots 116a extending in parallel, the curved track of which is shown in FIG. 7 in more detail. Movement of the curve plate 116 in the negative x-direction generates positive guiding of the guide members 113a configured as gliding pins which are fixedly connected with the pressing plate 113 (the second part of the pressing arrangement). Since the pins 113a are also guided by means of vertical guide sections 111c of the guide bases 111a of the supporting frame 111, a vertical movement of the pressing plate 113 is enforced. The force transmitted in the target position namely, at the height of the pins 113a, in the press-on position is in particular determined by the tension of the screwed springs 114 and the direction of the normal force at which the slide slots 116a of the curve plate 116 act on the pins 113a of the pressing plate 113. This press-on force acts in the pressing position of the pressing arrangement shown in FIG. 4b.

The spring components 143 (see FIG. 4c) shown in FIG. 4a must be removed mentally; in the arrangement of the pressing arrangement they should not be visible in FIG. 4a since they are arranged inside the hollow guide cylinders 146 (see FIG. 4c).

FIG. 4b shows in an isometric, exploded view the pressing arrangement of FIG. 4a in the second, lowered pressing position of the second component, the pressing plate 113. With its contact surface the pressing plate 113 sits on the target area which will be discussed later in respect of FIG. 4c. The guide pins 113a are accordingly positioned farther downwardly. Compared to the situation in FIG. 4a the curve plate 116 is displaced further in the negative x-direction. The guide pins 113a are therefore, relative to the FIG. 4a, located in a farther downwardly section of the curved tracks defined by the slide slots 116a. The bearing rod 118 is again displaced relative to the FIG. 4a farther in the negative x-direction, again urging the curve plate 116 in this direction via the tensioned screwed spring 114. The small gear wheel 133 has rotated ca. −240° counterclockwise relative to FIG. 4a so as to cause the indicated displacement of the bearing rod 118. Thus the force acting as a pressing force is transmitted by means of the gear transmission 130, the bearing rod 118, the screwed spring 114, and the curve plate 116, all of which are assigned to the transmission device, caused by the user's applying the excitation force and excitation movement to the lever 112.

FIG. 4c shows in an isometric, exploded view the structure of the second component 113 of the pressing arrangement of FIGS. 4a and 4b. The second component 113 is also shown at 140 and its sub-components, at 141 through 147. The second component 140 is a plate component comprising a primary segment 141 and a secondary segment 142. Such a segmental construction can certainly be realized in other embodiments of the invention as well. The primary segment 141 is presently a substantially square plate component. At the top edge of its lateral front faces pointing in the positive and negative y-directions it comprises the guide pins 144, 113a which pick up the force from the transmission component 116. The primary segment 141 has a substantially hollow interior for receiving the secondary segment 142 but in its top region it comprises above a horizontal intermediate plate a stabilizing honeycomb rib structure extending horizontally and connecting the interior sides of the outside surfaces of the primary segment 141. The rib structure improves the torsional stiffness of the primary segment 141 which is desirable in particular regarding the avoidance of the guide members 144, 113a canting when gliding in the slide slots 116a of the transmission component 116. Moreover the rib structure supports the four hollow guide cylinders 146 each of which receives and guides a guided, vertical pin component 147 fixedly connected with the secondary segment and an elastic spring component 143. The hollow guide cylinders 146 are open-bottomed and closed on top by an end wall which comprises an aperture 146a for the vertical pin components 147 to pass through which occurs at the latest as the pressing plate 140 is pressured. The planar contact area of the pressing plate 140 or the secondary segment 142 namely, the heated contact plate with which the pressing plate contacts the container top surfaces when the device is in operation, is not visible in the figures. The primary segment also serves the purpose of thermally insulating the heated contact plate from the ambience, in particular from the transmission component and the air in the interior of the cover. The pin components 147 engage in the apertures 146a with some play so as to allow a very minor inclination of the secondary segment 142 relative to the planar target area at the thermocycler. In this way the secondary segment 142 can be more uniformly pressed to the target area by means of an elastic spring device:

As is further shown in FIG. 4c, the primary segment 141 is coupled to the secondary segment 142 via an elastic spring device such that a pressing movement of the primary segment presses the secondary segment on. The elastic spring device comprises four elastic spring components 143. The pressing movement causes deformation of the elastic spring components. Providing the spring components causes uniformity of transmission of the pressing force of the second component to the target area. In this way the substantially planar contact surface of the second component or of the secondary segment rests in particular parallel and planar on the likewise substantially planar contact surface of the target area so as to cause the contact surfaces to be pressed uniformly. The force which the primary segment receives from the transmission device as the pressing force is that force which the secondary segment receives from the primary segment via the spring device and transmits to the target area as a pressing force. Therefore the spring device does not substantially complicate determining the desired function Fz(z) for the pressing force.

The secondary component 142 of the second component furthermore comprises a heating film and a temperature sensor (not shown) controlled via the flat ribbon cable 148 that is connected with a control device of the thermocycler. In this way the configuration of the cover of the thermocycler allows it to be tempered. The temperature of the contact region of the secondary component or of the cover can thus be controlled at 35° C. to 115° C., preferably between 95° C. and 105° C. In particular when the heating cover temperature is higher than that of the thermo block tempering the PCR samples in the containers, the contact of the higher-temperature contact region of the cover with the covering of the sample containers can prevent a condensation of sample vapors in the sample containers on the interior surface of the sample cover. This allows to maintain a constant concentration level of the PCR substances, in particular DNA fragments, in the samples, so as to render monitoring the PCR reactions more reliable.

As is further shown in FIG. 4c, the worktop section 150 of the thermocycler comprises the thermo block 152. It forms the receiving section for receiving up to 96 sample containers. It may e.g. be loaded with microtitration plates (96-well plates), PCR plates, or separate containers. A microtitration plate may be provided with a sealing film as a cover. Its top surface forms the target area for applying the pressing force Fz.

Figure 5A:
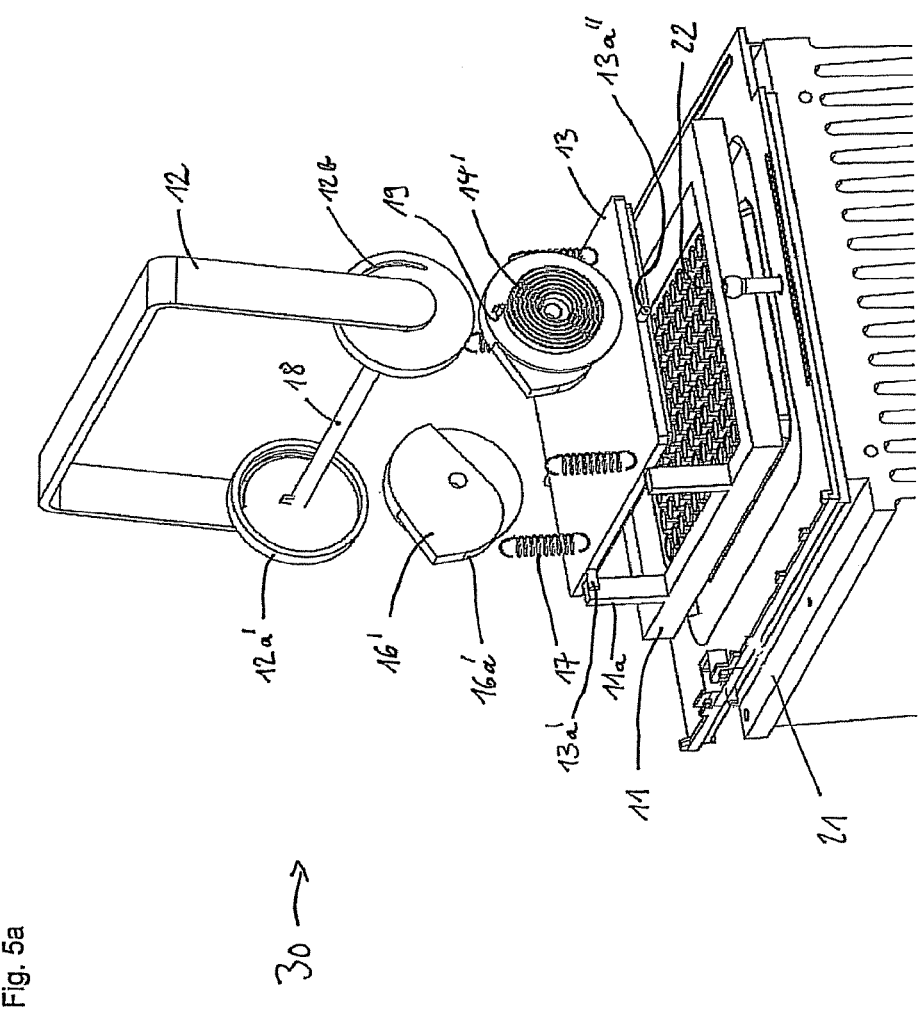
FIG. 5a shows in an isometric, exploded, oblique front view an exemplary embodiment of the pressing arrangement according to the invention according to the second preferred embodiment, in the first, lifted position of the second component.

FIG. 5a shows in an isometric, exploded, oblique front view the pressing arrangement 30 according to the second preferred embodiment, in the first, lifted position of the pressing plate. Instead of the curved track plate 16 the pressing arrangement 30 comprises an eccentric plate 16'. In the operating lever hub pre-stressed rotary springs 14' are mounted. These are clamped to one of the sides in the lever axle 18 of the operating lever 12 and to the other of the sides to a transmission pin 19 that is fixedly connected with the eccentric plate 16'. In this way the eccentric plate 16' is kinematically coupled with the operating lever 12. A circular plate 12a' is disposed in parallel to the eccentric plate 16', and disposed concentric with the operating lever hub 18 and fixedly connected with the operating lever 12. The circular plate 12a' comprises an elongated hole guide 12b in which the transmission pin 19 moves as the circular plate 12a' is rotated relative to the eccentric plate 16'. In FIG. 5a the elongated hole guide 12b abuts against the transmission pin 19 with its end closer to the lever.

The eccentric plate 16' comprises a circular base plate whose center lies in the operating lever hub 18. A section of the outside surface of the eccentric plate 16' is formed as an eccentric curve section 16a' defining a contacting and gliding surface 16a' extending radially outwardly, whose distance a from the operating lever hub 18 continuously changes with the rotational position ω, wherein the second derivative of the function a(ω) preferably does not equal zero. Rotating the eccentric plate 16' by means of the rotary spring 14' presses guided guide pins 13a" fixedly connected with the outside surface of the heating plate 13, downwardly.

The operating lever 12 and the pressing arrangement 30 are configured such that the user will always transfer the operating lever 12 from the same initial position namely, the third position as shown in FIG. 5a, to the same end position shown in FIG. 5b. Thus the excitation movement of the operating lever performed by the user is always the same movement. Again the user has the advantage that he does not need to concern himself with the "dosage" of the pressing force Fz since due to the specific pressing arrangement it will always be set automatically in dependence on the target position applied namely, in dependence on the height level of the microtitration plate (not shown) in the thermo block 22. In the second preferred embodiment of the pressing arrangement 30 according to the invention this is achieved by the sequences of movement and transmissions of force described below:

In the upright position of the operating lever 12 (third position) in FIG. 5a the gliding surface 16a' of the eccentric plate 16' contacts the guide pin 13a" of the heating plate 13 firstly in a contact point starting position that is located closer to the operating lever hub 18 than is the contact point end position in FIG. 5b in which the operating lever 12 lies horizontal. Coupling the rotary spring to the operating lever hub and the eccentric plate 16' firstly causes a vertically downwardly movement of the heating plate 13 or its guide pins 13" in a first section of the pivoting movement of the operating lever 12 until the heating plate 13 hits on the microtitration plate in the thermo block 22 in the target position. While the heating plate 13 is descending, the lever 12 keeps abutting the elongated hole guide until the heating plate 13 is stopped in the target area of a microtitration plate. Substantially only friction forces and restoring forces of the restoring springs 17 need to be overcome. While pressure is applied to the target area by means of the heating plate 13 the curved track 16a' of the eccenter 16' is leading in front of the stopper of the transmission pin in the rotary elongated hole guide 12b. In this way the spring torque of the slightly expanding rotary spring 14' (relatively constant for all the target positions) acts directly on the eccentric 16' and is not discharged at the base 21 via the operating lever and its necessary arresting.

As the operating lever is opened again, the rotary spring 14 is first tensioned by the amount of the arc length by which the eccenter 16' was leading. Now as the rotational elongated hole guide 12b is in abutment against the transmission pin, the lever opening movement is transmitted to the eccentric 16', which is lifted. Additionally the heating plate is guided vertically by way of vertical guiding means 11a, 13a'. Furthermore the heating plate 13 needs to be lifted again in opening. This is done by the restoring springs 17. The restoring springs 17 showing a small spring constant also serve the purpose to lift the heating plate 13 to effect permanent abutment to the eccentric curve section 16a'. The restoring springs may be replaced by a positive guide similar to the slide slots in FIGS. 4a-c.

Figure 6A:
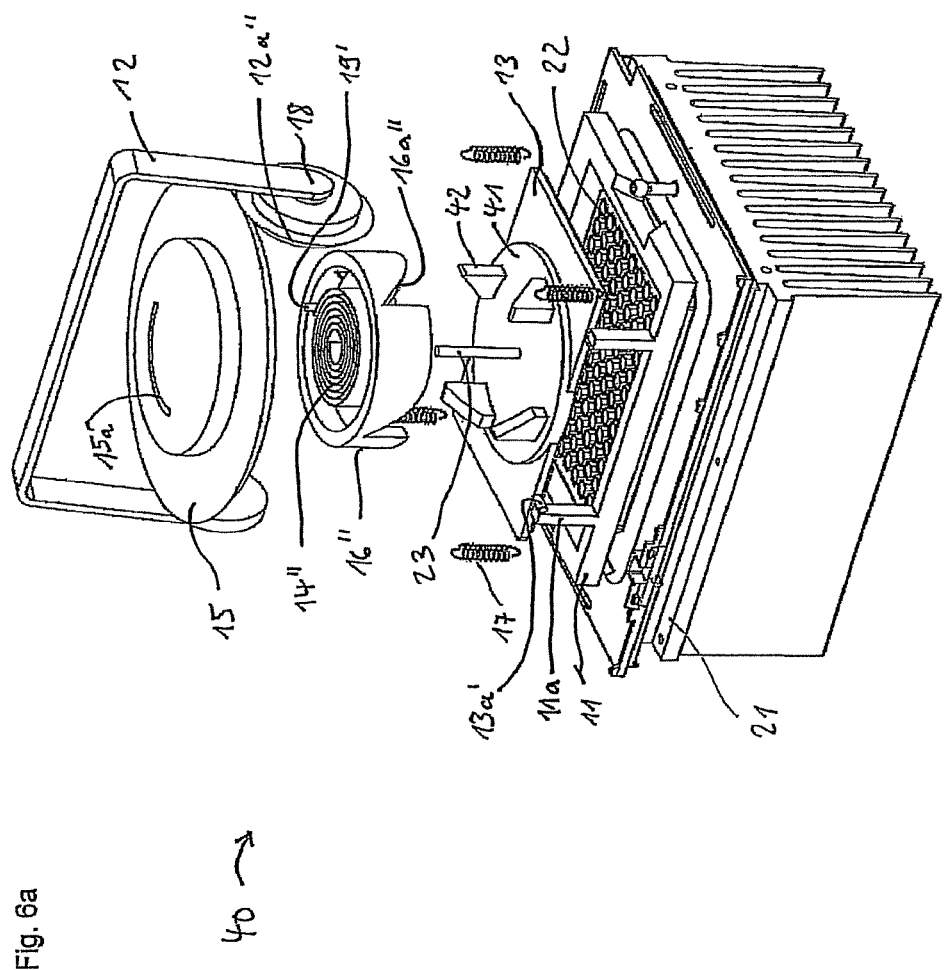
FIG. 6a shows in an isometric, exploded view an exemplary embodiment of the pressing arrangement according to the invention according to the third preferred embodiment, in the first, lifted position of the second component.
Figure 6B:
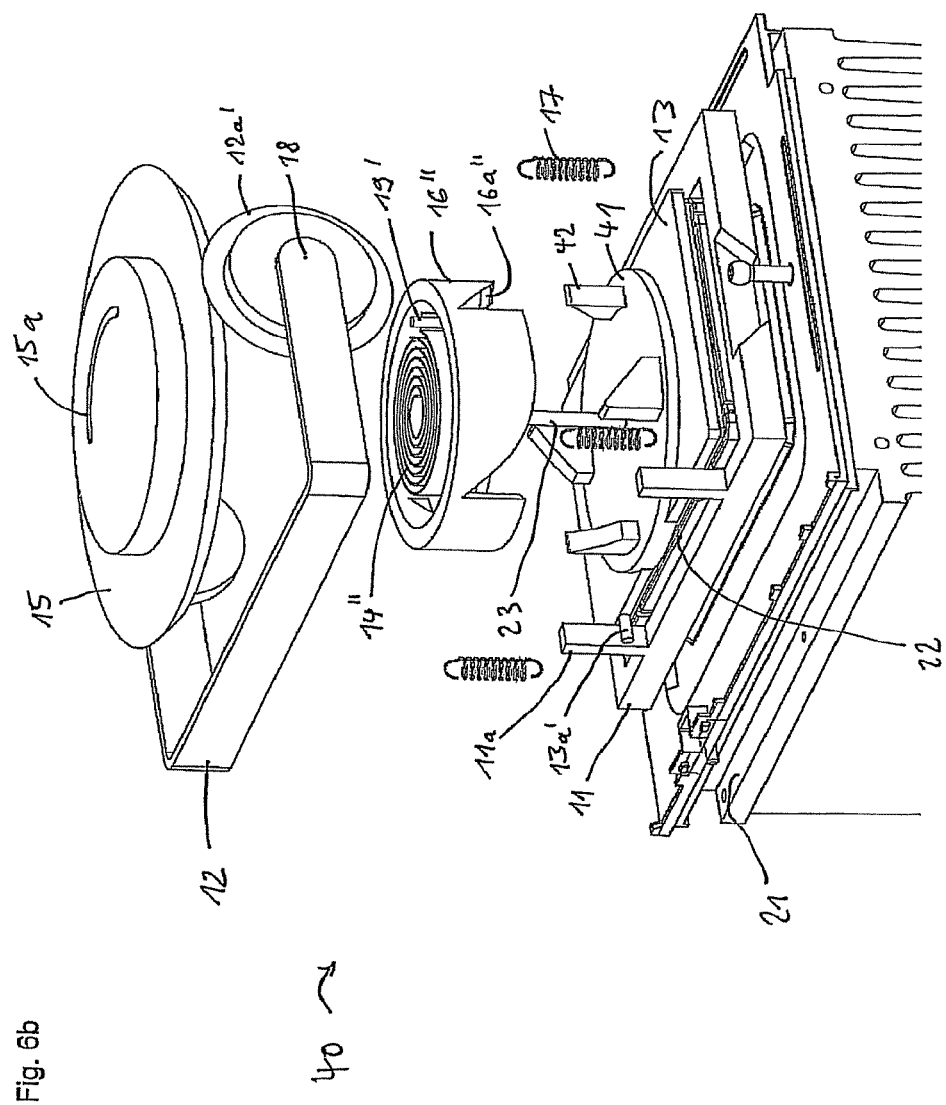
FIG. 6b shows in an isometric, exploded view the pressing arrangement of FIG. 6a, in the second, lowered pressing position of the pressing plate.

FIG. 6a shows in an isometric, exploded view the pressing arrangement 40 according to the third preferred embodiment in the first, lifted position of the pressing plate. A second transmission component is presently a disk section 16" supported horizontally rotationally about the vertical rotational axis having a multiple-pitch thread whose four threads 16a" are shaped eccentrically, thus showing a pitch changing at least in sections. The tensioning member 14" is presently a rotary spring 14" supported horizontally rotationally. At one of its ends it is connected with a transmission pin 19' which is presently fixedly connected with the disk section 16" and at the other of its ends, with the disk section 16".

Application of the force by the pressing arrangement 40 is similar to the case of the pressing arrangement 30 in FIGS. 5a, 5b. The excitation movement originating from the operating lever 12 in the pressing arrangement 40 is firstly deflected via the disk section 12a" fixedly connected with the lever 12 and carrying a beveled gear wheel (not completely visible), and via the beveled gear wheel disposed on the outside of the disk 15, to the disk 15 which is supported horizontally rotatably on the supporting frame 11. The rotary excitation movement of the lever 12 in the x-z-plane is transformed to an intermediate movement of the disk 15 in the x-y-plane.

Introduction of force in turn occurs via a rotary spring 14" disposed kinematically between the driven gear wheel 15 and the transmission component 16". To this end the disk 15 comprises the elongated hole guide 15*a* extending concentrically about the vertical rotational axis 23. In this guide the guide pin 19' of the rotary spring 14" is guided until it abuts the end of the elongated hole guide such that further rotation of the disk 15 causes deflection and tensioning of the rotary spring 14". The rotary spring 14" is thus tensioned by the driven gear wheel 15 and rotates the first transmission component 16". The latter transmits the movement or force via the four curved tracks 16*a*" of the four thread pitches to four transmission components 42 which are configured integrally with the second transmission component 41. The second transmission component 41 is fastened to the heating plate 13 and disposed linearly translationally movable with it relative to the supporting frame 11 and in the z-direction. The rotation of the first transmission component 16" changes the contact point at the curved track of a thread pitch 16*a*" with the transmission component 42. A rotation of the first transmission component 16" therefore causes downwardly movement of the second transmission component 41 which by way of the pressing force Fz is pressed to the heating plate 13 which in turn presses downwardly toward the stop position. The heating plate itself needs to be secured against rotation in the x-y-plane by means of the guide 11*a*, 13*a'*. Restoring the heating plate while the operating lever is opened in turn occurs by the restoring springs 17, which may, however, as was e.g. described above, solved in another way.

The pressing arrangement 40 is again configured such that the user will always transfer the operating lever 12 from the same initial position namely, the third position, to the same end position (fourth position). The excitation movement of the operating lever performed by the user is thus again always the same movement in the third preferred embodiment. The user has again the substantial advantage that he does not need to concern himself with the "dosage" of the pressing force Fz since due to the specific pressing arrangement it will always be set automatically in dependence on the target position applied namely, in dependence on the height level of the microtitration plate in the thermo block 22.

FIG. 7 shows the transmission member according to an exemplary embodiment of the pressing arrangement according to the invention which is in particular employed in the exemplary embodiment of FIGS. 4*a*, 4*b*, 4*c*. In this transmission component 16 the path of a curved track was determined and specified by calculation. This applies likewise to the corresponding curved tracks of the curved track components in the embodiments of FIGS. 5*a* and 5*b*, respectively 6*a* and 6*b*. Compared to FIGS. 4*a*-4*c* the x-axis in FIG. 7 extends in the opposite direction. A curved track plate 16 disposed upright is visible. The curved track plate 16 is disposed on the supporting frame 11 horizontally movable in the x-direction by way of the guide slots 16*e* in the lower region of the curve plate 16 and by way of the guide pins 11*e* of the supporting frame and is substantially not movable in the y- and z-directions relative to the supporting frame 11. A force Fx transmitted to the curved track plate by the extension spring 14 in the x-direction moves the curved track plate in the (positive) x-direction (presently: to the right), enforcing downward movement of the positively guided guide member 13*a* that is fixedly connected with the heating plate 13.

The curved track plate 16 is presently configured such that the pressing force Fz transmitted to the heating plate 13 shows a specific dependence on the target position z. To this end the curved track has an upper curve segment in the region 16*a*1 and a lower curve segment in the region 16*a*2.

In the lower curve segment, microtitration plates showing different, relatively low heights (e.g. TT-skirted and TT-semiskirted) are served which ideally ought to be subjected to the same, rather high force. Only higher containers (e.g. 0.5-ml containers) are subjected to a lower force. The steeper upper curve section serves for this purpose. In the topmost curved guide section in the region 16*a*3 the curved track is flatter, thus showing a lower gradient than in the region 16*a*1. The transition of the steeper section 16*a*1 to the flatter region 16*a*3 facilitates restoring the lever 12, perceptibly to the user, to the position shown in FIG. 4*a* in which the guide pins 13*a* are disposed in the topmost region 16*a*3. The distance 16*a*1 in FIG. 7 corresponds to approximately 6.9 mm and it may generally be e.g. between 4 to 8 mm. The final position in 16*a*3, "lever open", is e.g. at 9.5 mm (starting from the dashed line between 16*a*2 and 16*a*1). The height of the curved track in the region 16*a*2 is approximately 7.1 mm and may generally be e.g. between 4 to 8 mm. The height of the curved track in the region 16*a*3 is approximately 3.1 mm and may generally be e.g. between 2 to 4 mm. The illustration in FIG. 7 is to scale such that any further preferred dimensions may be taken from the figure. Such a curved track allows to approach e.g. container heights showing height differences of the top container surfaces (stop position, "target area") in respect of the base of the apparatus of a maximum of e.g. 24 mm for applying a pressing force determined by the curved track in dependence on such height. This maximum height difference may be different, it may preferably lie between 0.5 cm and 5 cm between 1 cm and 4 cm, between 1.5 cm and 3.5 cm or between 2.0 cm and 3.0 cm.

For the lower curve segment 16*a*2 the following applies: Since the curved track plate will be displaced to the right if the microtitration plate is of low height, the spring 14 will expand. This is intended to be compensated by corresponding adaptation of the angle α in the slide element. For the containers to be subjected to the same force Fz in the lower curve segment independently of their heights, the following, calculated curve z(x) of the lower curve segment can be derived as indicated in equation (10). Moreover one can determine from the equation (7) the force path Fz(z) if the functions z(x) or x(z) of the curved track path are known. Moreover one can determine from equation (9) the required curved track z(x) for any random desired function Fz(z) of the pressing force:

(1) $F_z = F_x / \tan(\alpha)$     inclined plane (2) $\tan(\alpha) = dz/dx$     tangent angle (3) $F_z = F_x * \dfrac{dx}{dz}$     (2) in (1)

(4) $F_x = c * \Delta L$     Hookean law     $\Delta L$: tension length of spring $c$: spring constant (5) $\Delta L = x + \Delta L_0$     $\Delta L_0$: spring preload (6) $F_x = c * (x + \Delta L_0)$     (5) in (4)

(7) $F_z = \dfrac{c * (x + \Delta L_0) * dx}{dz}$     (6) in (3)

-continued (8) $dz = \dfrac{c*(x+\Delta L_0)}{F_z} * dz$ (9) $z = \int \dfrac{c*(x+\Delta L_0)}{F_z} dx$ (9) $z = \left[\dfrac{c*\Delta L_0 * x}{F_z} + \dfrac{c*x^2}{2*F_x}\right]$ for $F_z = const$

(10) $z = \dfrac{c}{F_z} * \left[\Delta L_0 * x + \dfrac{1}{2}x^2\right]$

The invention claimed is:

1. A laboratory apparatus having a pressing arrangement for a cover of the laboratory apparatus, for pressuring a second component against a sample area of the laboratory apparatus to be covered, the pressing arrangement having at least:
a first component disposed to exert an excitation force,
a second component formed to be a plate component movably disposed to exert a pressing force Fz in different target positions,
a transmission device disposed for transmitting a force from the first component to the second component,
characterized in that
the transmission device comprises a transmission component disposed to be driven by the first component and to drive the second component,
the transmission device comprising an elastic tensioning member being a spring and the transmission component, to which the first component is connected and which is coupled to the spring, the spring being disposed to be driven by the first component so as to change the tension of the spring and to drive the transmission component such that the transmission component is driven by the spring, which transforms the force transmitted by the elastic tensioning member and transmits it to the second component as a transformed force being the pressing force, and the transmission component causes a setting of the pressing force Fz in dependence on the target position,
wherein the transmission device comprises at least one transformer section which is formed at the transmission component and which is formed to be a curved guide section of the transmission component and which transforms a force transmitted by the elastic tensioning member and transmits the force to the second component as a transformed force,
and wherein the curved guide section of the transmission component comprises a curved-track shaped design which serves to guide a guided component along such curved track,
the pressing arrangement comprising a guiding device by means of which the second component is guided between a first and second position along a linear vertical direction.

2. The laboratory apparatus according to claim 1, characterized in that the first component, the second component and the transmission component are disposed on the pressing arrangement to be movable relative to one another, the second component being movably disposed at the pressing arrangement for performing a pressing movement between a first position p1 and a second position p2, starting out from the first position up to a stop position of the second component, the stop position being in particular that position in which the second component is blocked in at least one direction in the pressing movement of the second component.

3. The laboratory apparatus according to claim 2, characterized in that the pressing movement is a linear, downwardly movement, which is a movement in the negative direction of the z-axis of a Cartesian coordinate system.

4. The laboratory apparatus according to claim 2, characterized in that the curved guide section is configured such that in different target positions z of the second component the pressing force Fz shows a specified amount, which is determined by a configuration of the curved guide section and which follows the function Fz(z) at least in sections.

5. The laboratory apparatus according to claim 4, characterized in that the guide section comprises a first curved guide section and a lower curved guide section and the transformer section defines the first curved guide section and the lower curved guide section, comprising a first curved track section fz1(x, y) and co-determining a first function Fz1(z) and defining a second curved guide section, and an upper curved guide section, comprising a second curved track section fz2(x, y) and co-determining a second function Fz2(z) wherein a gradient in each position in the second curved guide section is larger than or equal to a gradient in each position in the first curved guide section and in the lower curved guide section, which means d/dx (fz2(x, y))>=d/dx (fz1(x, y)).

6. The laboratory apparatus according to claim 5, characterized in that the first curved guide section is shaped to co-determine a first function Fz1(z) such that the force Fz1(z1) is constant.

7. A cover of a thermocycler, for pressuring a second component against a sample area of a laboratory apparatus to be covered, wherein the cover comprises
a pressing arrangement, the pressing arrangement comprising:
a first component disposed to exert an excitation force,
a second component formed to be a plate component movably disposed to exert a pressing force Fz in different target positions,
a transmission device disposed for transmitting a force from the first component to the second component,
characterized in that
the transmission device comprises a transmission component disposed to be driven by the first component and to drive the second component,
the transmission device comprising an elastic tensioning member being a spring and a transmission component, to which the first component is connected and which is coupled to the spring, the spring being disposed to be driven by the first component so as to change the tension of the spring and to drive the transmission component such that the transmission component is driven by the spring, which transforms a force transmitted by the elastic tensioning member and transmits it to the second component as a transformed force being the pressing force,
and the transmission component causes a setting of the pressing force Fz in dependence on the target position,
wherein the transmission device comprises at least one transformer section which is formed at the transmission component and which is formed to be a curved guide section of the transmission component and which transforms the force transmitted by the elastic tensioning member and transmits the force to the second component as a transformed force, and wherein the curved guide section of the transmission component comprises a curved-track shaped design which serves to guide a guided component along such curved track, the pressing arrangement comprising a supporting device and a guiding device connected therewith by means of which the second component is guided between a first and second position at the supporting device along a linear vertical direction.

8. The laboratory apparatus of claim 1, which is a thermocycler.

9. A method for pressuring a component against a target area by means of a laboratory apparatus, the laboratory apparatus having a pressing arrangement for a cover of the laboratory apparatus, for pressuring a second component against a sample area of the laboratory apparatus to be covered, the pressing arrangement having at least:

a first component disposed to exert an excitation force, a second component formed to be a plate component movably disposed to exert a pressing force Fz in different target positions, a transmission device disposed for transmitting a force from the first component to the second component, the transmission device comprising a transmission component disposed to be driven by the first component and to drive the second component, the transmission device comprising an elastic tensioning member being a spring and the transmission component, to which the first component is connected and which is coupled to the spring, the spring being disposed to be driven by the first component so as to change the tension of the spring and to drive the transmission component such that the transmission component is driven by the spring, which transforms the force transmitted by the elastic tensioning member and transmits it to the second component as a transformed force being this pressing force, and the transmission component causes a setting of the pressing force Fz in dependence on the target position, wherein the transmission device comprises at least one transformer section which is formed at the transmission component and which is formed to be a curved guide section of the transmission component and which transforms a force transmitted by the elastic tensioning member and transmits the force to the second component as a transformed force, and wherein the curved guide section of the transmission component comprises a curved-track shaped design which serves to guide a guided component along such curved track, the pressing arrangement comprising a guiding device by means of which the second component is guided between a first and second position along a linear vertical direction, the method comprising the steps, in variable sequence:

transferring the second component to a target position;

exerting an excitation force by means of the first component;

transmitting the force from the first component to the second component by means of the transmission device so as to exert a pressing force by means of the second component;

driving the transmission component by means of the first component and driving the second component by means of the transmission component;

causing a tension change of the at least one elastic tensioning member by way of driving the first component;

driving the transmission component by means of the at least one elastic tensioning member, applying the pressing force Fz in dependence on the target position of the second component.

10. The laboratory apparatus of claim 1, characterized in that the curved guide section comprises a curved-track shaped design according to one of the following configurations: a curved track-shaped projection, surface or edge, a curved track-shaped depression or slot, a pivoted link, an eccentric member or a variable-pitch thread.

11. The laboratory apparatus of claim 1, which is a thermostat.

* * * * *